US006451593B1

(12) United States Patent
Wittig et al.

(10) Patent No.: US 6,451,593 B1
(45) Date of Patent: Sep. 17, 2002

(54) DESIGN PRINCIPLE FOR CONSTRUCTION OF EXPRESSION CONSTRUCTS FOR GENE THERAPY

(75) Inventors: Burghardt Wittig; Claas Junghans, both of Berlin (DE)

(73) Assignee: Soft Gene GmbH, Berlin (DE)

( * ) Notice: Subject to any disclaimer, the term of this patent is extended or adjusted under 35 U.S.C. 154(b) by 0 days.

(21) Appl. No.: 09/310,842

(22) Filed: May 12, 1999

Related U.S. Application Data

(63) Continuation-in-part of application No. PCT/DE97/02704, filed on Nov. 13, 1997.

(30) Foreign Application Priority Data

Nov. 13, 1996 (DE) .......................................... 196 48 625

(51) Int. Cl.$^7$ .......................... C12N 15/00; C12N 5/00; C12P 21/06; C07H 21/00; A01N 43/04
(52) U.S. Cl. ................... 435/320.1; 435/69.1; 435/325; 435/455; 536/23.1; 536/23.5; 514/44
(58) Field of Search .............................. 536/23.1, 23.5; 435/320.1, 325, 69.1, 455; 514/44

(56) References Cited

U.S. PATENT DOCUMENTS

| 5,580,859 A | 12/1996 | Felgner et al. ................ 514/44 |
| 5,584,807 A | 12/1996 | McCabe ..................... 604/71 |
| 5,589,466 A | 12/1996 | Felgner et al. ................ 514/44 |

FOREIGN PATENT DOCUMENTS

| EP | 0686697 | 12/1995 |
| EP | 0732395 | 9/1996 |
| WO | 9626270 | 8/1996 |
| WO | 9632473 | 10/1996 |

OTHER PUBLICATIONS

Eck, et al., 1996. Goodman & Gilman's The Pharmacological Basis of Therapeutics, Ninth Edition. McGraw–Hill, New York.*
Johnston, et al., 1993. Genetic Engineering, 15:225–236.*
"Immunization by Direct DNA Inoculation Induces Rejection of Tumor Cell Challenge" Wang et al., Human Gene Therapy 6:407–418 (Apr. 1995).
"Identification of Wild–Type and Mutant p53 Peptides Binding to HLA–A2 Assessed by a Peptide Loading–Deficient Cell Line Assay and Novel Major Histocompatibilty Complex Class I Peptide Binding Assay" Stuber et al., Eur. J. Immunol. 1994. 24:765–768.
"Particle–Mediated Gene Transfer of Granulocyte–Macrophage Colony–Stimulating Factor cDNA to Tumor Cells: Implications for a Clinically Relevant Tumor Vaccine" Mahvi et al., Human Gene Therapy 7:1535–1543 (Aug. 20, 1996).

"Ex Vivo Regulation of Specific Gene Expression by Nanomolar Concentration of Double–Stranded Dumbbell Oligonucleotides" Clusel et al., Nucleic Acids Research, 1993, vol. 21, No. 15, 3405–3411.
"Dendritic Cells as Initiators of Tumor Immune Responses: A Possible Strategy for Tumor Immunotherapy?" Grabbe et al., Immunology Today, vol. 16, No. 3 1995, 117–121.
"Sequence–Independent Inhibition of RNA Transcription by DNA Dumbbells and Other Decoys" Lim et al., Nucleic Acids Research, 1997, vol. 25, No. 3, 575–581.
"A New Peptide Vector for Efficient Delivery of Oligonucleotides into Mammalian Cells" Morris et al., Nucleic Acids Research, 1997, vol. 25, No. 14, 2730–2736.
"Improved Biological Activity of Antisense Oligonucleotides Conjugated to a Fusogenic Peptide" Bongartz et al., Nucleic Acids Research, 1994, vol. 22, No. 22, 4681–4688.
"The Influence of Endosome–Disruptive Peptides on Gene Transfer Using Synthetic Virus–Like Gene Transfer Systems" Plank et al., The Jornal of Biological Chemistry, vol. 269, No. 17, Apr. 29, pp. 12918–12924, 1994.
"Linear Mitochondrial DNAs of Yeasts: Closed–Loop Structure of the Termini and Possible Linear–Circular Conversion Mechanisms" Dinouel et al., Molecular and Cellular Biology, Apr. 1993, pp. 2315–2323.
"Heterologous Protection Against Influenza by Injection of DNA Encoding a Viral Protein" Ulmer et al., Science, vol. 259, Mar. 19, 1993, pp. 1745–1749.
"Comparison of Organic Monolayers on Polycrystalline Gold Spontaneously Assembled from Solutions Containing Dialkyl Disulfides or Alkanethiols" Biebuyck et al., Langmuir 1994, 10, 1825–1831.
"Regression of Established Murine Carcinoma Metastases Following Vaccination with Tumour–Associated Antigen Peptides" Mandelboim et al., Nature Medicine, vol. 1, No. 11, Nov. 1995, pp. 1179–1183.

* cited by examiner

*Primary Examiner*—Scott D. Priebe
*Assistant Examiner*—Sumesh Kaushal
(74) *Attorney, Agent, or Firm*—Nils H. Ljungman & Associates

(57) ABSTRACT

The invention concerns an expressible nucleic acid construct, which contains only the sequence information necessary for expressing a gene for RNA or protein synthesis. Expression constructs of this type can be used in gene therapy and genetic vaccination and avoid many of the risks associated with constructs today. The invention further concerns the possibility of improving the conveying of the construct into cells or tissue by covalent linkage of the construct, for example to particles or peptides.

32 Claims, 2 Drawing Sheets

DESIGN PRINCIPLE FOR CONSTRUCTION OF EXPRESSION CONSTRUCTS FOR GENE THERAPY

CONTINUING APPLICATION DATA

This application is a Continuation-In-Part application of International Application No. PCT/DE97/02704, filed on Nov. 13, 1997, which claims priority from Federal Republic of Germany Patent Application No. 196 48 625.4, filed on Nov. 13, 1996. International Application No. PCT/DE97/02704 was pending as of the filing date of the above-cited application. The U.S. was an elected state in International Application No. PCT/DE97/02704.

BACKGROUND OF THE INVENTION

1. Field of the Invention

The invention concerns a design principle for a minimalistic expression construct which contains no genetic information other than the information to be expressed, apart from promotor and terminator sequences which are necessary for the control of expression. Such minimal expression constructs are to be used for molecular-medical applications, specifically genetic vaccination, tumor therapy, and -prophylaxis.

The design principle is to be used for the construction of expression constructs for the expression of MHC-I or MHC-II presentable peptides, cytokines, or components of the regulation of the cell cycle, or for the synthesis of regulative RNA molecules and antisense RNA, ribozyme or mRNA-editing-RNA. Furthermore, an important aspect of the invention is that the construction principle allows for the covalent linking of the expression construct, e.g. with peptides, proteins, carbohydrates or glycopeptide ligands, as well as particles which allow for the transfer of the constructs into cells by ballistic transfer especially into dermis, muscle tissue, pancreas, and the liver.

2. Background Information

The invention is to be used especially in two related fields: somatic gene therapy and genetic vaccination. These two meet in the field of immuno gene therapy of oncological conditions. Whereas classical gene therapy intends to substitute missing or defective genes, immuno gene therapy intends to activate the immune system of the patient against tumor specific antigens. In malignant melanoma and some other tumors, a number of tumorspecific antigens have been identified which can be recognized by cytotoxic T-lymphocytes (Van den Eynde B. and Brichard V. G., Current Opinion in Immunology (1995) 7: 674–681). In most cases these are fragments of mutated proteins, which are either relevant for tumor development and promotion, or are fragments of proteins from a changed metabolism of the tumor cell (Stüber et al., Eur. J. Immunol. (1994) 24: 765–768). In the case of melanoma, the presented peptides often derive from proteins from the melanocyte-specific differentiation. Approaches which make use of the activation of the immune system against such tumor specific antigens are in need of methods which enable the antigenic epitopes to be overexpressed in non-tumor cells, such as antigen-presenting cells (macrophages, dendritic cells). Alternatively, genes which control the expression of peptide-presenting proteins, such as CIITA or ICSBP are of great importance.

Laboratory experiments and clinical studies, in which such peptides have been used for the induction or amplification of a tumor specific cytotoxic response, concentrate on conventional vaccination protocols, in which the corresponding peptides are being used (Strominger J., Nature Medicine, (1995) 1:1.179–1.183). Alternatively, antigen-presenting cells such as dendritic cells, were incubated with high concentrations of such peptides. Thereby, the peptides originally present on the MHC-complex were exchanged for tumor specific peptides (Grabbe et al., Immunology Today (1995) 16:117–121).

The term genetic vaccination (immunization) describes the utilization of an experimental finding which first was debated as a scientific artefact, but has recently been corroborated in a number of biomedical problems (Piatak et al., Science 259 (1993): 1745–1749). If an expression plasmid for mammalian cells is injected into skin or muscle, there is, albeit in very low efficiency, an expression of the corresponding gene close to the injection site. If the expression product is a protein alien to the organism (xenogenic or allogenic protein), uptake and presentation of fragments of the expressed protein (oligopeptide) by antigen-presenting cells (APC) takes place, probably by way of local inflammation, Depending on local cytokine patterns and the type of cells in which the plasmid is expressed (presentation by MHC-I or MHC-II), there is an induction of an immune reaction along the $T_{H1}$ or $T_{H2}$ pathway (Wang et al., Human Gene Therapy 6 (1995): 407–418), which eventually leads to the proliferation of cytotoxic T-cells or to the production of soluble antibodies. The transfection of dendritic cells with expression constructs for antigenic peptides ex-vivo is included in the term genetic vaccination in this context (Schadendorf et al. Molecular Medicine Today, 2 (1996); 144–145).

Such genetic vaccination avoids the numerous risks of conventional immunization approaches. Many approaches are known in gene therapy that are designed to effect therapeutic or prophylactic effects by the transfer of genetic information into cells. These approaches have not only been demonstrated in animal experiments, but also in numerous clinical studies in patients, an example being the so-called ballisto magnetic vector system (EP0686697 A2) for the transfection of conventional, plasmid-based expression constructs. The ballisto magnetic vector system was employed by the inventors of this application in three clinical phase I/II studies for the production of interleukin-7 (IL-7), interleukin-12 (IL-12) or granulocyte-macrophage-colony stimulating factor (GM-CSF) expressing tumor cells. In the case of expression of IL-12, separate expression constructs for the genes of the two IL-12 subunits were transferred ballisto-magnetically at the same time.

With the maturing of this new discipline, however, the methodological repertoire for gene therapy demands critical inspection. A fundamental aspect of this question is the sequence information contained in conventionally employed DNA constructs . If such expression constructs are to be employed in a great number of patients, and possibly more than once, safety aspects, especially those related to immunological concerns, will come to bear heavily. The conventionally used expression constructs are derivatives of eucaryotic expression plasmids. These have two fundamental disadvantages: their size, which inhibits fast transport into the cell's nucleus, and the presence of sequences which are not needed for the intended use. Expression constructs used so far contain constitutively expressed genes, i.e. for resistance against cytostatica which serve as selection markers, and in some cases sequences for the episomal replication in the target cell. The expression of these genes leads to an unwanted background of transfected genetic information. Furthermore, apart from the promotor-geneterminator structure which is to be expressed, these constructs carry at least the sequences needed for bacterial replication, since the plasmids are propagated in bacteria. These sequences are not needed for the intended use, either.

It is obvious that conventional expression constructs lead not only to the expression of the desired gene, but also to the biosynthesis of xenogenic proteins, even if their prokaryotic promotors show very low activity in mammalian cells. With longer or repeated application it can be assumed that the desired immune response is masked by such contaminating gene products, and significant immunological complications can occur.

Another problem in the application of gene therapeutic methods concerns the method by which the genetic material to be transferred is brought into the cell. For reasons of efficiency, immunological safety, and broad applicability across a wide spectrum of cell types, the method of ballistic transfer is preferred. A fundamental advantage of ballistic transfer, compared to alternative transfection methods, is that the method is applicable across a broad spectrum of different cells or tissues. Another disadvantage of methods currently used for the transfection of eukaryotic cells, such as electroporation or lipofaction, is that the treatment brings the substance to be transported only across the plasma membrane, the first barrier, which shields the cell from its environment. However, for most substances interacting with the regulative function of the cell, it is important to get from the cytoplasma across the nuclear membrane into the nucleus. This membrane is biophysically fundamentally different from the plasma membrane, and methods such as electroporation or lipofection do not lead to a passage through this membrane. The reason why these methods nonetheless lead to expression of recombinant nucleic acid constructs transfected into the cells in a part of the cell population, is the fact that in the act of cell division, the nuclear membrane is rendered permeable. In consequence, methods such as-electroporation or lipofaction only lead to transfection of cells which divide. Therefore these methods are not applicable to the transfection of many slowly or non-dividing cells, which can be interesting in the context of gene therapy, such as stem cells of the immune system or the heamatopoietic system, muscle cells, cells of exocrine or endocrine organs and their accompanying cells. The also commonly used and very efficient transfection method of retroviral transport of genetic material suffers the great disadvantage of targeting the tranfected cells for a possible cytotoxic reaction by the host organism, which probably limits the applicability of this method for gene therapeutic approaches.

The method of ballistic transfer has been used for the ex-vivo treatment of autologous and allogenic patient cells (Mahvi et.al.; Human Gene Therapy 7 (1996): 1535–43). However, when treating cells in tissue, a method which should be advantageous especially for the oncotherapeutic treatment of solid tumors or the mass prophylaxis against infections by genetic vaccination, the state of the art has disadvantages: The method of ballistic transfer makes use of DNA adsorbed to microprojectiles. When transfecting skin or other tissues, the penetration depth of the DNA constructs is lower than the penetration depth of the projectiles. DNA is desorbed soon after impact on the tissue. Only the uppermost tissue layer in the direction of the projectiles is transfected, although the projectiles themselves enter much deeper into the tissue. When transfecting solid tumor tissue (colon carcinoma, rectum carcinoma, reno-cell carcinoma and others), it has been found that, with suitable adaption of the parameters, the microprojectiles enter up to five cell layers deep into tissue slices. The transfected cells, however, (visible as fluorescent cells when transfected with a recombinant expression construct containing a green fluorescent protein from aequrea sectoria) were all found in the uppermost cell layer facing the impact of the microprojectiles. A more stable coupling of the DNA constructs to the surface of the microprojectiles would be desirable in order to avoid the desorption of the substance to be transported. In this way only, the application of gene therapeutic approaches to solid tumors would be realistic, since only the transfection of tumor slices in the depth of the tissue enables a sufficient number of treated cells to be achieved. It is also imaginable that a combination of different coupling protocols enables the release of different genetic information within the same cell population at different timepoints. For these and numerous other applications, microparticles which bring the substance to be transported all the way into the hit cell and then make the substance available to the cell, would be very desirable.

U.S. Pat. No. 5,584,807 (McCabe) describes an instrument in form of a gas pressure operated gun for the introduction of genetic material into biological tissue, in which gold particles are used as carrier material for the genetic information, without making reference to the nature of the genetic material in particular. U.S. Pat. Nos. 5,580,859 and 5,589,466 (Felgner) describe a method for the introduction of DNA into mammalian cells in the context of gene therapy. Naked DNA sequences coding for physiologically active proteins, peptides or polypeptides and are under the control of a promotor are injected directly into cells. Naked DNA refers to sequences that are free of other genetic material like viral sequences. DNA is expressed in these cells and serves as vaccine.

WO 96/26270 (Rhône-Poulenc Rorer S. A.) describes a circular double-stranded (supercoiled) DNA molecule, containing an expression cassette coding for a gene and controlled by a promoter and a terminator. This system is employed in vaccination in the context of gene therapy, also.

EP 0 686 697 A2 (Soft Gene) concerns a method for the enrichment of cells modified by ballistic transfer, and describes the technological background, the related problems, and the solutions found so far. The basic method of ballistic transfer is described herein. A device useful for the execution of this method is described in EP 0 732 395 A1.

The ballistic particles are gold particles with a diameter of either 1 $\mu$m or 1.5 $\mu$m (EP 0 686 697 A2), chosen depending upon the cell type. These gold particles are coated with superparamagnetic particles of roughly 30 nm diameter. The superparamagnetic particles at the same time furnish a useful surface for the coating with biomolecules. The use of magnetic particles enables subseqent separation.

Furthermore, dumbbell-shaped nucleic acid constructs are known that are characterized by the following features: They are short (10–50 bp double-stranded DNA) nucleic acid constructs, which were made for structure research or as double-stranded oligomers with improved nuclease resitence used for scavenging of sequence specific DNA ligands (Clusel et. al.; Nucleic Acids Res. 21 (1993): 3405–11; Lim et. al., Nucleic Acids Res. 25 (1997): 575–81).

Longer DNA molecules, which can exist throughout parts of their replication cycles as dumbbells, are known in nature as mitochondrial genomes of some species, such as ciliatae and yeasts (Dinuel et. al., Molecular and Cell Biology, 13 (1993): 2315–23). These molecules are about 50 kb in size and have a very complex genetical structure. Likewise, a closed covalent linear structure is known from vaccinia virus.

Peptide-nucleic acid-linkages with localization sequences are known for short DNA oligomers. Morris et al. . (Nucleic Acids Res. 25 (1997): 2730–36) describe the coupling of oligomers 18–36 base pairs in length, with a 27 amino acid residues containing peptide, which contains the nuclear localization sequence from SV40 as well as a signal peptide from HIV-gp41 responsible for the fusion with CD4-positive cells.

The use of peptide chains for crossing the endosomal membrane has been investigated by several groups. The 23 N-terminal amino acids of haemagglutinine were adsorbed by non-covalent interactions to expression plasmids in order to facilitate the uptake of these complexes into the cytosol after endosomal uptake (Plank et.al., J.Biol.Chem.269, 12918, (1994)). The covalent attachment of antisense desoxyoligonucleotides to haemagglutinine peptide is described by Bongartz et al. (Nuc.Acids Res. 22, 4681, 1994).

OBJECT OF THE INVENTION

Based on this state of the art, it is the objective of the invention presented here to develop an expression construct that contains only the information necessary to be expressed, and to provide means for the transport into a cell, which is to be treated therapeutically.

SUMMARY OF THE INVENTION

This objective is reached using the features of claims 1 and 13. According to the invention, double-stranded DNA-expression constructs, which are to be transported, are modified in such fashion that both anti-parallel strands of the DNA-polymer, containing the coding sequence and the promotor and terminator sequences necessary for its expression, are linked by loops of single stranded desoxyribonucleotides at both ends in such a way, that a continuous covalently closed molecule results. Preferably, said loop contains 3 to 7 nucleotides. In FIG. 1, such a construct is shown schematically. Such expression constructs are employed for the expression of MHC-I or MHC-II presentable peptides, cytokines, or components of the regulation of the cell cycle, or for the synthesis of regulative RNA-molecules, such as antisense-RNA, ribozymes or mRNA-editing RNA. Since the nucleic acid is covalently closed on both ends and no free hydroxyl-groups are available for nucleolytic cleavage, the molecule has a much higher stability against intra- and inter-cellular nucleases, and thus a longer halftime in the body or the cell. This advantage is especially important in the application in-vivo.

To explain, an objective can be reached using, a deoxyribonucleic acid construct for transcription of RNA-molecules. This construct can comprise a circular strand of desoxyribonucleic acid comprising a partly complementary, antiparallel base sequence, so that a dumbbell-shaped construct is formed, in which the complementary antiparallel base sequence essentially comprises a promotor sequence, a coding sequence and a polyadenylation signal or another RNA-stabilizing signal. The non-complementary sequence comprises two loops of single-stranded deoxyribonucleic acid, which covalently join the 5'- and 3'-ends of the complementary, antiparallel strands. A microprojectile for ballistic transfer of the deoxiribonucleic acid constructs into cells can be characterized by that its material being gold, oxide ceramic, glass ceramic or glass and the nucleic acid to be transported can be bound covalently by thiole- or disulfide moyeties, ester-, amide-, aldimine-, ketale- or acetale- or ether functionalities to the microprojectile.

While it is an object of the present invention to develop an expression construct that contains only the information necessary to be expressed, however, depending upon the methods and materials used, in at least one embodiment of the present invention, the expression construct may possibly contain substantially only, essentially only, and/or virtually only the information necessary to be expressed. In at least one emodiment these expression constructs can be developed, for example, for the expression of MHC-I or MHC-II presentable peptides, cytokines, or components of the regulation of the cell cycle, or for the synthesis of regulative RNA molecules and anti-sense RNA, ribozyme or mRNA-editing RNA.

Furthermore, according to the invention, said loop linking the strands can contain one or more modified bases, said bases containing chemical function, which allow the coupling of the molecule with a solid base, preferably amino-, carboxylic acid-, thiol-, or disulfide-modifications. Said modifications are covalently linked by known synthetic steps with corresponding carboxylic acid-, aldehyde-, amine-, thiole-, or other functions, or directly with a gold surface of a microprojectile for ballistic transfer. It can be imagined that a combination of different linking methods facilitates the release of a plurality of genetic information within the same cell population at different timepoints.

Apart from the aspect of easier chemical linking to the surface of the micro-projectile, said nucleic acid construct presents another advantage: nucleic acid constructs currently used in transfection in gene therapy, are produced in bacteria and carry, besides the sequences relevant in context of their therapeutical use, other sequences, which are only needed for the amplification of the nucleic acid constructs in bacteria. These sequences are an unknown risk for the patient who is to be treated, as it is not known whether and how these affect the organism. Such sequences, which not solely serve the primary objective of transfection in the target cells, can be excised from nucleic acids amplified in bacteria by restriction endonuclease digestion prior to transfection, and can be substituted by covalent linkage of short ends of desoxyribonucleic acid, said ends possibly being modified. According to another aspect of the invention, DNA to be transported into the cell can be obtained by polymerase chain reaction with chemically modified primers, so that the products of the polymerase chain reaction contain the chemical modifications needed for binding to the micro-projectile. An advantage of the construction principle according to the invention over current expression vectors is, that the resulting constructs contain only the sequence needed for the expression of the target gene.

Another aspect of the invention is that a loop of single stranded desoxyribonucleotides on either end of the molecules allows for the introduction of chemical modifications in such a way that non-nucleic acid ligands can be covalently linked to the nucleic acid expression construct. This way for example, peptides needed for the nuclear localization of the expression constructs can be linked to the construct in such a way, that after entering the cytosol of a cell said construct is transported by the translocation apparatus of the cell into nuclear compartments where it can be transcribed. Thereby, the constraints mentioned above concerning some transfection methods would be dealt with. Likewise the direct linking of the construct to peptides-, glycopeptide-, or carbohydrate-ligands which facilitate the entrance of the construct by cell-specific surface receptors is facilitated.

Specifically, according to the invention, double-stranded anti-parallel DNA expression constructs are modified in such a way that the ends of the double strands each contain a disulfid bridge linking the strands on both ends over covalently bonded alkyl groups bound to the 5'-end of one strand and the 3'-end of the other strand.

Any eucariotic promoter sequence can be employed for the control of transcription of the expression plasmid. Especially advantageous are short promoters with a high transcription rate transcribable in a multitude of cells, e.g. the "immediate early promotor" from cytomegalo virus (CMV) promoter RNA-polymerase III-depending promoters such as the 7SK-promoter or the U6-promoter are of advantage for the transcription of genes coding for RNA. Such promoter sequences can result in the expression of short antisense-RNAs, ribozymes, and artificial mRNA in vivo. RNA-polymerase III produces significantly more copies of RNA than polymerase II and has an exact termination signal, a feature of special advantage. Said promotor sequences are characterized by their shortness, leading to small corresponding dumbbell expression constructs, a feature favourable to the entry of said expression constructs into the cell's nucleus.

The invention also concerns the transport of nucleic acids into cells. According to the invention, nucleic acids are transferred into cells by linking the nucleic acids to the surface of the micro-projectile carrying the nucleic acids into cells by adsorption, covalent or ionic interaction, in such a way that said nucleic acids are not or not completely desorbed upon passage of the micro-projectile through connected tissue into tissue fluid or cell layers, but remain inked to the microprojectiles until said microprojectiles come to rest with said nucleic acids in the target cells. This has the advantage that the substance is provided to a cell either in its bound state, or is desorbed in a process slow in comparison to the time of entry and is provided to the cell in a desorbed state, depending on the mode of binding.

The binding of thioles or disulfides to gold surfaces is well researched and described (G. M. Whitesides et al., Langmuir 10 (1994): 1825–1831). The nucleic acids to be transported are adsorbed preferably to micro-projectiles made of gold, however, by providing the nucleic acids with thiole or disulfide groups by covalent modification with publicly available reagents, and then adsorbed through their thiole or disulfide groups, or covalently bound to the micro-projectile by anodic oxidation of the thiole or disulfide functions employing the gold of the micro-projectile as anode. According to the invention, the substance to be transported is bound by sulfur-gold linkage or by disulfide linkage to the micro-projectile. When employing micro-projectiles made of gold, the substance to be transported is modified by molecules containing thiole groups or disulfide bridges, if it does not already contain thiole or disulfide groups able to bind by themself. Said substance is then bound to the gold surface of the micro-projectile by chemisorption. The resulting gold-sulfur linkage is sufficiently strong to carry the molecules to be transported through several cell layers.

Since the cell contains molecules comprising thiole groups, above all the ubiquitous glutathion, an equilibrium reaction of the thiole groups on the gold surface leads to the slow desorption of the chemisorbed molecule from the surface of the micro-projectile. Thereby, the transported substance is freely available to the cell after desorption. Furthermore, according to the invention, when employing micro-projectiles made of gold, the molecule to be transported containing thiole or disulfide bridges can be bound covalently to the micro-projectile by anodic oxidation of the thiole or disulfide functions employing the gold micro-projectile as anode.

According to the invention, when employing micro-projectiles made of oxidic ceramics, glass ceramic, or glass, the molecule to be transported is bound by ester, amide, aldimine, ketal, acetal or ether linkage, or other functionalities known to the organic chemist for binding of molecules to a solid surface. The numerous silane reagents used for the modification of silicon oxide phases can be employed here.

The invention is used for ex-vivo gene therapy. Preferably, interleukin-7 (IL-7) SEQ ID NO: 5 and interleukin-12 (IL-12), SEQ ID NO: 2 and SEQ ID NO: 4 proteins and their subunits are expressed, as are interleukines, granulocyte-makrophage-colony-stimulating factor (GM-CSF) SEQ ID NO: 3, cell surface antigens and ligands of immune controlling or modifying lymphocyte antigens like CD40, B7-1, and B7-2, proteins of the MHC-complexes I or II or β-2 microglobulin, interferone consensus sequence binding protein ICSBP, CIITA, Flt3, or entire proteins or fragments thereof of presentable epitopes from tumor specific expressed mutated or non-mutated proteins, e.g. Ki-RAS-fragments, p16 and p53, or bcr-abl (SEQ ID NO: 1) product. The use of micro-projectiles which are all linked with constructs of the same type is preferred, but cocktails (mixtures) of micro-projectiles which are each linked to different constructs are possible, as are micro-projectiles which are each linked with a cocktail of different constructs.

The desoxyribonucleic acid construct according to the invention is preferably employed as vaccine for the treatment of infectious diseases in humans and animals, e.g. malaria and influenza.

More advantageous features are contained in the subclaims.

The above discussed embodiments of the present invention will be described further hereinbelow with reference to the accompanying figures. When the word "invention" is used in this specification, the word "invention" includes "inventions", that is, the plural of "invention". By stating "invention", the Applicants do not in any way admit that the present application does not include more than one patentably and non-obviously distinct invention, and maintain that this application may include more than one patentably and non-obviously distinct invention. The Applicants hereby assert that the disclosure of this application may include more than one invention, and, in the event that there is more than one invention, that these inventions may be patentable and non-obvious one with respect to the other.

BRIEF DESCRIPTION OF THE DRAWINGS

The invention is depicted in the attached figures and is described more closely in the following examples.

FIG. 1.2. shows the functional structure of one of several possible expression constructs;

DESCRIPTION OF THE PREFERRED EMBODIMENT

EXAMPLE 1

[Synthesis of the Expression Constructs]

The fundamental construction principle is depicted schematically in FIG. 2 and is as follows:

1.1 Synthesis from Vector

Figure 1:
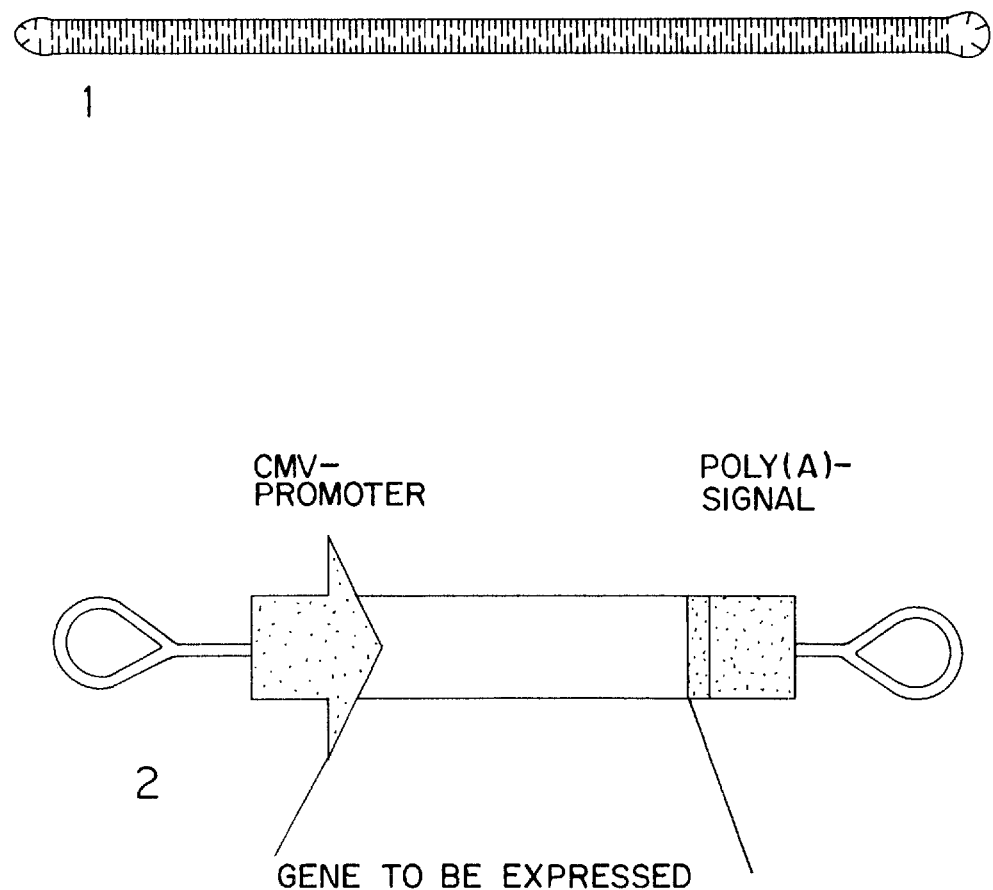
FIG. 1 shows a schematic outline of the construction concept, whereas FIG. 1.1. shows the confirmation of the covalently closed phosphate-sugar-backbone; the number of base pairs depicted does not necessarily show the length of the constructs but only serves as example of the principle.
Figure 2:
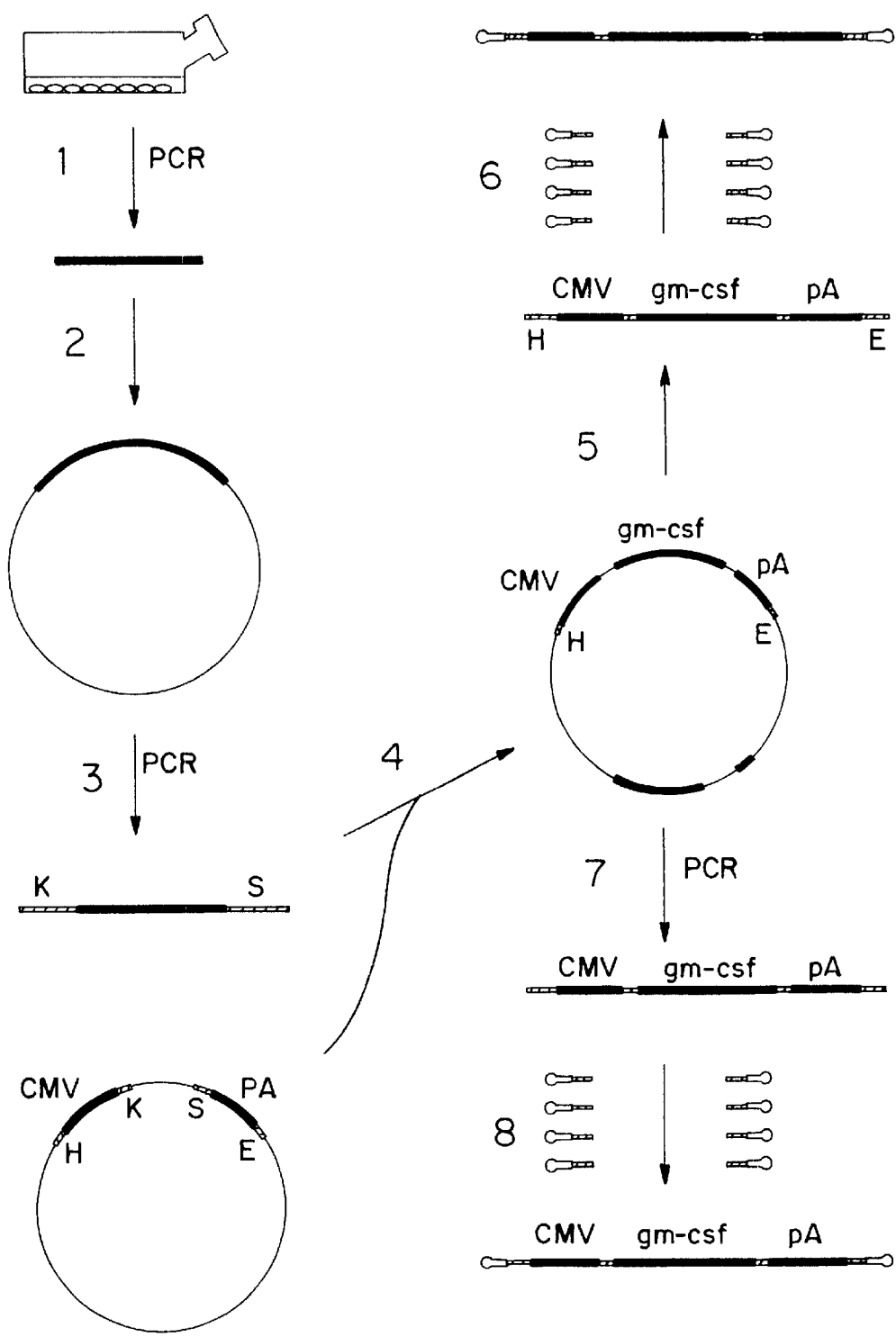
FIG. 2 shows the synthesis of the constructs schematically.

The gene to be expressed, e.g. granulocyte-macrophage stimulating factor (GM-CSF), is amplified from cDNA using suitable primers by PCR (FIG. 2(1)) and recombined into a suitable plasmid vector (FIG. 2(2)). After sequencing and confirmation of the target sequence, the sequence to be expressed is amplified from said plasmid vector by means of two primer sequences (oligodesoxynucleotides carrying on the 5'-end of their sequence restriction enzyme recognition sites) (FIG. 2(3)). The resulting amplification product is digested with said endonucleases, for which a recognition site was provided on said primers. After isolation of the amplified fragment from an agarose-gel, said fragment is recombined into an expression plasmid, which is amplifiable in bacteria, and in which the gene to be expressed is located in the desired orientation in the context of the sequences controlling expression contained in said expression plasmid (FIG. 2(4)).

Said expression plasmid is amplified in bacteria and isolated according to methods known in the art. After digestion with restriction endonucleases, the recognition sites of which are flanking the sequence which is to be contained in the dumbbell-shaped expression constructs, the restriction fragments are separately isolated by methods of anion exchange chromatography (FIG. 2(5)), and are subsequently ligated to hairpin-forming self-hybridizing oligodesoxynucleotides (short DNA-molecules obtained by automated chemical DNA synthesis, which can form stem-loop-structures based on their self-complimentarity; these molecules will later form the covalently closed ends of the dumbbell-shaped DNA-molecules), which contain an single-stranded overlap compatible with the overlap of the construct obtained by the digestion with endonucleases (FIG. 2(6)). After separation of excess hairpin desoxynucleotides by anion exchange chromatography, the constructs according to the invention are obtained.

1.2. Synthesis from PCR-product

Alternatively, the construct is amplified directly by polymerase chain reaction, the primer oligodesoxynucleotides carrying recognition sites for restriction endonucleases on the 5-prime ends of their sequence (FIG. 2(7)). After separation of the primers by anion exchange chromatography, the resulting amplificate is digested with said endonucleases, for which a recognition sequence was provided on said primer oligodesoxynucleotides. After separation of the smaller restriction fragments, the construct is ligated to short hairpin-formed self-hybridizing oligodesoxynucleotides, said hairpin-formed desoxynucleotides providing a overhang able to hybridize to the overhang resulting from the restriction enzyme digestion of the construct (FIG. 2(8)). After separation of excess hairpin-desoxyoligonucleotides by anion exchange chromatography, the constructs according to the invention are obtained.

An expression construct consisting of the sequence for gm-csf under control of the "early immediate promotor" from CMV and the polyadenylation sequence from SV40, was obtained from plasmid mtv-GM-CSF by complete digestion with EcoRI and HindIII. The smaller fragment (1290 bp) was isolated by anion exchange chromatography (stationary phase Merck fractogel EMD-DMAE; 25 mM Tris/HCl pH8; 0–1 M NaCl), and after concentration and desalting, was ligated with a 200-fold excess of 5' phosphorylated hairpin-desoxyribonucleotides AATTCG-GCCGGCCGTTTTCGGCCGGCCG (SEQ ID NO:6) and AGCTTGGCCGGCCGTTTTCGGCCGGCCA (SEQ ID NO:7) (TIB Molbiol, Berlin) in the presence of 25 U/ml T4-DNA-ligase overnight at room temperature. The reaction was stopped by heating to 60° C. The construct ligated to the desoxyoligoribonucleotide was separated from excess desoxyoligoribonucleotide by anion exchange chromatography, concentrated by ethanol precipitation, dissolved in water and applied to sterile primary colon carcinoma cells using the ballistic transfer according to a published method.

EXAMPLE 2

[In vivo Expression]
Ballistic Transfer of GM-CSF into K562

30 μl of a suspension of gold particles (1.6 μm diameter, supplied by Bio-Rad, Hercules, Calif., USA, concentration of the suspension: 30 mg/ml) are transferred to a macro carrier-polymer sheet (Bio-Rad). The gold is allowed to sediment, and the supernatant is cautiously removed. Onto the wetted surface, 30 μl of a 1+3 mixture of a suspension of colloidal magnetic particles (mean diameter 65 nm; Miltenyi GmbH, Bergisch-Gladbach, Germany; used as supplied; concentration unknown) and GM-CSF-expression-dumbbell-construct (example 1) are pipetted. The sedimented gold is re-suspended in said mixture and allowed to re-sediment. The supernatant liquid is removed and the gold particles are allowed to dry. 300 μl polylysine are transferred to the center of a petri-dish (3.5 cm), allowed to rest for 30 min and washed off with PBS-medium. 100,000–200,000 cells (erytroleukemia cell line K562) are transferred onto the polylysine-coated surface of the petri-dish in 300 μl RPMI-medium (10% FCS), and allowed to rest for 10 min. 2 ml RPMI-medium (10% FCS) are added, and the cells are incubated 1–2 h in an incubator.

Ballistic transfer is conducted according to the manufacturers with a Biolystic PDS 1000/C (Bio-Rad, Hercules, Calif., USA). The rupture disk employed corresponds to a pressure of 1100 psi. The pressure of the vacuum cell is 508 mm Hg. Magnetic separation is conducted as published (EP 0732 395A1); control of successful transfection is performed by GM-CSF-ELISA. The manufacturer's (Bio-Rad's) instructions and/or directions for the Biolystic PDS 1000/C are incorporated by reference, as if set forth in there entirety herein.

EXAMPLE 3

[Example for Synthesis of a Expression-construct with Nuclear Localization Sequence]

An expression construct consisting of the gene for a green fluorescent protein under control of the early immediate promoter from CMV and the polyadenylation sequence of SV40 (pEGFP, Clontech Inc.) was obtained by restricition enzyme digestion with EcoRI and HindIII. The smaller fragment was isolated by anion exchange chromatography (stat.phase: Merck Fractogel EMD-DMAE; 25 mM Tris/HCl pH 8; 0–1M NaCl) and ligated after concentration and desalting with a 200-fold molar excess of 5'-phosphorylated hairpin-desoxyoligoribonucleotides AATTCGGCCGGC-CGTXTCGGCCGGCCG (SEQ ID NO: 6) and AGCTTG-GCCGGCCGTXTCGGCCGGCCA (SEQ ID NO: 7) in the presence of 25 u/ml T4-DNA-Ligase overnight at room temperature (X signifies the peptide modification: Amino-Uracil coupled to the peptide by amide function (TIB-Molbiol, Berlin)) The reaction was stopped by heating to 60° C. The construct ligated to the amino-desoxy-uracil-modified desoxyoligonucleotide was separated from excess hairpin desoxynucleotides by anion exchange chromatography, concentrated by ethanol precipitation and dissolved in water. 1 μg of the thiol-modified construct was incubated with 1 mg micro-projectiles (spherical gold, mean diameter 1 μm, Bio-Rad, Hercules, Calif.) in water over night at room temperature. The gold particles were washed twice with water and applied to adherent ceratinocytes with the ballistic transfer according to the known procedure.

EXAMPLE 4
[Synthesis of Nucleic-acid-modified Gold Particles]

An expression construct, which consists of the sequence for gm-csf under control of the "early immediate promoter" from CMV and the polyadenylation sequence from SV40 was excised from the plasmid mtv-gmcsf by complete digest with EcoRI and HindIII. The smaller fragment (1290 bp) was isolated by anion exchange chromatography (stat. phase: Merck Fractogel EMD-DMAE; 25 mM Tris/HCl pH 8; 0–1 M NaCl) and following concentration and desalting ligated to a 200-fold molar excess of 5'phosphorylated hairpin desoxyoligoribonucleotides AATTCGGCCGGC-CGTXTCGGCCGGCCG (SEQ ID NO:6) and AGCTTG-GCCGGCCGTXTCGGCCGGCCA (SEQ ID NO:7) (X specifies the thiol modifier C6 S—S (TIB-Molbiol, Berlin)) in the presence of 25 u/ml T4 DNA Ligase and incubated over night at room temperature. The reaction was stopped by heating to 60° C. The construct ligated to the thiol desoxyribonucleotide was separated from excess thiol modified desoxyribonucleotide by anion exchange chromatography, and resolved in water. 1 μg of the thiol modified construt was incubated over night with 1 mg microprojectiles (shperical gold, mean diameter 1 μm, Bio-Rad, Hercules, Calif.) in water. The gold particles were washed twice with water and used for ballistic transfer into sterile primary coloncarcinoma cells (see Expl. 5).

EXAMPLE 5
[Ballistic Transfer to Solid Tumor Tissue]

Sterile primary colon carcinoma tissue was removed surgically and cooled on ice. Necrotic parts and connective tissue is removed as much as possible. Pieces of ca. 1 cm$^2$ surface are excised from the tumor, washed in ice-cold PBS and fixated on the sample holder of a tissue slicer (vibratome 1000 sectioning system; TPI, St. Louis, Mo.) with tissue glue. The tumor is sliced into slices of 500 μm thickness. The slices are stored in ice-cold PBS and transfected as soon as possible. 30 μl of a suspension of GM-CSF-expression construct-coated gold particles and colloidal magnetic particles (mean diameter: 65 nm—Miltenyi GmbH, Bergisch-Gladbach) are pipeted onto a macro carrier polymer sheet (Bio-Rad). The gold is allowed to sediment, the supernatant removed and the gold particles are allowed to dry. The procedure of ballistic transfer is identical with the procedure described in example 2. Both sides of the tumor slice are transfected. After transfection, the slice is passed twice through a cell sieve, and the cells are separated as described.

Magnetic separation is performed according to the published protocol (EP 0 732 395 A1); the success of the transfection is controlled by GM-CSF-ELISA.

EXAMPLE 6
[Synthesis of Nucleic Acid-modified Aluminum Particles]

5 μg of an expression construct consisting of the gene for a green fluorescent protein under control of the early immediate promoter from CMV and the polyadenylation sequence of SV40 (pEGFP, Clontech Inc.) was obtained by restricition enzyme digestion with EcoRI and HindIII. The smaller fragment was isolated by anion exchange chromatography (stat.phase: Merck Fractogel EMD-DMAE; 25 mM Tris/HCl pH 8; 0–1M NaCl) and ligated after concentration and desalting with a 200-fold molar excess of 5'-phosphorylated hair-pin-desoxyoligoribonucleotides AATTCGGCCGGC-CGTYTCGGCCGGCCG (SEQ ID NO:6) and AGCTTG-GCCGGCCGTYTCGGCCGGCCA (SEQ ID NO:7) (Y signifies the carboxylic acid modified thymidinedesoxynucleotide (TIB-Molbiol, Berlin)) in the presence of 25 U/ml T4-DNA-Ligase overnight at room temperature.

1 g aluminiumoxyde particles (mean diameter 1.0 μm) were refluxed in a solution of tri-etoxaminopropylsilane in toluene (2%) overnight. The solid matter is filtrated, washed with toluene and ethanol, dried and ground. 5 mg of the resulting amino-modified aluminiumoxyde are reacted in 100 ml aqueous carbonate buffer (pH 8.0) with 4 μg of the carbonic-acid-modified construct in the presence of 50 μM 1-ethyl-3-(3-dimethylaminopropyld)carbodiimide and 50 mM N-hydroxysuccinimide for 2 h at room temperature. The resulting nucleic-acid modified microparticles can be transported to cells by acceleration in a suitable apparatus, as described in DE 195 10 696 and EP 0 732 395 A1, whereby the information contained in the transported constructs is made available to the cells.

One feature of the invention resides broadly in a deoxyribonucleic acid construct for transcription of RNA-molecules, characterized by a circular strand of desoxyribonucleic acid comprising a partly complementary, antiparallel base sequence, so that a dumbbell-shaped construct is formed, in which the complementary, antiparallel base sequence in the essential comprises a promotor sequence, a coding sequence and a polyadenylation signal or another RNA-stabilizing signal, and the non-complementary sequence comprises two loops of single-stranded deoxyribonucleic acid, which covalently join the 5'- and 3'-ends of the complementary, antiparallel strands.

Another feature of the invention resides broadly in a deoxyribonucleic acid construct characterized by that said loops consisting of three to seven nucleotides, and in which one or several of said nucleotides are covalently modified by carboxylic acid-, amine-, thiole- or aldehyde functionalities.

Yet another feature of the invention resides broadly in the deoxyribonucleic acid construct characterized by that said chemically modified nucleotides is being linked to a peptide leading to the directed transport of the construct into the nucleus.

Still another feature of the invention resides broadly in the deoxyribonucleic acid construct characterized by that said chemically modified nucleotides is being linked to a peptide enabling liberation of the construct from the endosome.

A further feature of the invention resides broadly in the deoxyribonucleic acid construct characterized by using a 7SK promoter as said promoter.

Another feature of the invention resides broadly in the deoxyribonucleic acid construct characterized by using a CMV promoter as said promoter.

Yet another feature of the invention resides broadly in the deoxyribonucleic acid construct coding for interleukine-7.

Still another feature of the invention resides broadly in the deoxyribonucleic acid construct coding for interleukine-12 or one or several of its constituting subunits.

A further feature of the invention resides broadly in the deoxyribonucleic acid construct coding for gm-csf.

Another feature of the invention resides broadly in the deoxyribonucleic acid construct coding for p16 or p53 protein or fragments thereof.

Yet another feature of the invention resides broadly in the desoxyribonucleic acid construct coding for peptide fragments of mutated ki-ras, mutated p53 or bcr-abl translocation product with a length of between 10 and 100 aminoacids.

Still another feature of the invention resides broadly in the microprojectile for ballistic transfer of deoxyribonucleic acid constructs into cells in which the substance to be transported is linked by adsorption or covalent or ionic binding in such a way to said microprojectile that the substance to be transported upon passage of the microparticle through connective tissue, the extracellular liquid or cell layers is not or not completely desorbed, but remains bound to said microprojectile until the substance to be transported rests along with said microprojectile in the target cell.

A further feature of the invention resides broadly in the microprojectile characterized by that its material being gold, oxide ceramic, glass ceramic or glass and said nucleic acid to be transported is bound covalently by thiole- or disulfide moyeties, ester-, amide-, aldimine-, ketale- or acetale- or ether functionalities to said microprojectile.

Another feature of the invention resides broadly in the microprojectile characterized by that said microprojectile being made out of an electrically conducive material and said nucleic acid being linked to said microprojectile by electrochemically coupling of disulfide or thiole moieties, employing the microprojectile as electrode.

Yet another feature of the invention resides broadly in the microprojectile characterized by that said microprojectile being of the size of 0.3 micro meters to 3 micro meters.

Still another feature of the invention resides broadly in the use of a nucleic acid construct in ex-vivo gene therapy.

A further feature of the invention resides broadly in the use of a microprojectile in ex-vivo gene therapy.

Another feature of the invention resides broadly in the use of said deoxyribonucleic acid constructs as vaccine for prevention of infectious disease in humans or animals.

All, or substantially all, of the components and methods of the various embodiments may be used with at least one embodiment or all of the embodiments, if any, described herein.

The corresponding foreign and international patent publication applications, namely, Federal Republic of Germany Patent Application No. 196 48 625.4, filed on Nov. 13, 1996, and DE-OS 196 48 625.4 and DE-PS 196 48 625.4, and International Application No. PCT/DE97/02704, filed on Nov. 13, 1997, as well as their published equivalents, namely, WO 98/21322 published on May 22, 1998, and other equivalents or corresponding applications, if any, in corresponding cases in the Federal Republic of Germany and elsewhere, and the references cited in any of the documents cited herein, are hereby incorporated by reference as if set forth in their entirety herein.

Complete names and/or references for abbreviations used in this application may be found in the following documents—in U.S. Patent Numbers: U.S. Pat. No. 5,679,553 entitled "Process for rendering a nucleic acid amplification reaction product incapable of being a target for further amplification, a diagnostic assay employing said process"; U.S. Pat. No. 5,624,803 entitled "In vivo oligonucleotide generator, and methods of testing the binding affinity of triplex forming oligonucleotides derived therefrom"; U.S. Pat. No. 5,889,169 entitled "Cell cycle regulatory protein p16 gene"; U.S. Pat. No. 5,858,679 entitled "Method for determining the presence of functional p53 by measuring GADD45 protein expression"; U.S. Pat. No. 5,726,024 entitled "p53as protein and antibody therefor"; U.S. Pat. No. 5,679,641 entitled "Peptides of human P53 protein for use in human T cell response inducing compositions, and human P53 protein-specific cytotoxic t-lymphocytes"; U.S. Pat. No. 5,362,623 entitled "Sequence specific DNA binding by p53"; U.S. Pat. No. 5,672,473 entitled "Methods of identifying compounds useful for treating autoimmune diseases"; U.S. Pat. No. 5,831,064 entitled "Kaposi's sarcoma-associated herpes virus (KSHV) interferon consensus sequence binding protein (ICSBP) and uses thereof"; U.S. Pat. No. 5,707,803 entitled "DNA regulatory elements responsive to cytokines and methods for their use"; U.S. Pat. No. 5,693,522 entitled "Anti-cancer immunotherapeutics"; U.S. Pat. No. 5,476,995 entitled "Peptide production"; U.S. Pat. No. 5,149,628 entitled "Methods for detecting bcl-3 gene in human leukemias"; U.S. Pat. No. 5,763,573 entitled "GTPase activating protein fragments"; U.S. Pat. No. 5,760,203 entitled "Gap gene sequences" U.S. Pat. No. 5,604,099 entitled "Process for detecting specific nucleotide variations and genetic polymorphisms present in nucleic acids"; U.S. Pat. No. 5,582,995 entitled "Methods of screening for compounds which inhibit the direct binding of Ras to Raf"; U.S. Pat. No. 5,741,650 entitled "Methods for detecting colon cancer from stool samples"; U.S. Pat. No. 5,670,325 entitled "Method for the detection of clonal populations of transformed cells in a genomically heterogeneous cellular sample"; U.S. Pat. No. 5,652,222 entitled "Selective inhibition of leukemic cell proliferation by bcr-abl antisense oligonucleotides"; U.S. Pat. No. 5,369,008 entitled "Methods for the detection of BCR-ABL and abnormal ABL proteins in leukemia patients"; U.S. Pat. No. 5,863,794 entitled "SV40 viral vectors for targeted integration into cells"; U.S. Pat. No. 5,858,705 entitled "Polynucleotides encoding human DNA ligase III and methods of using these polynucleotides"; U.S. Pat. No. 5,847,083 entitled "Modified p53 constructs which enhance DNA binding"; U.S. Pat. No. 5,843,423 entitled "Methods of stimulating hematopoietic cells with flt3-ligand"; U.S. Pat. No. 5,635,388 entitled "Agonist antibodies against the flk2/flt3 receptor and uses thereof"; U.S. Pat. No. 5,554,512 entitled "Ligands for flt3 receptors"; U.S. Pat. No. 5,843,882 entitled "Antiviral proteins and peptides"; U.S. Pat. No. 5,462,854 entitled "Inverse linkage oligonucleotides for chemical and enzymatic processes"; U.S. Pat. No. 5,874,082 entitled "Humanized anti-CD40 monoclonal antibodies and fragments capable of blocking B cell proliferation"; U.S. Pat. No. 5,849,898 entitled "CD40 coding sequences"; U.S. Pat. No. 5,677,165 entitled "Anti-CD40 monoclonal antibodies capable of blocking B-cell activation"; U.S. Pat. No. 5,877,021 entitled "B7-1 targeted ribozymes"; U.S. Pat. No. 5,747,034 entitled "Methods and materials for the induction of T cell anergy"; U.S. Pat. No. 5,738,852 entitled "Methods of enhancing antigen-specific T cell responses"; U.S. Pat. No. 5,869,050 entitled "Methods of blocking T-cell activation using anti-B7 monoclonal antibodies"; U.S. Pat. No. 5,861,310 entitled "Tumor cells modified to express B7-2 with increased immunogenicity and uses therefor"; U.S. Pat. No. 5,869,241 entitled "Method of determining DNA sequence preference of a DNA-binding molecule"; U.S. Pat. No. 5,726,014 entitled "Screening assay for the detection of DNA-binding molecules"; U.S. Pat. No. 4,760,022 entitled "Stabilized plasmids"; U.S. Pat. No. 5,777,074 entitled "Human monoclonal antibodies directed against the transmembrane glycoprotein (GP41) of human immunodeficiency virus-1 (HIV-1); U.S. Pat. No. 5,753,503 entitled "Human monoclonal anti-HIV-I-antibodies"; U.S. Pat. No. 5,736,391 entitled "HIV gp41 mutants"; U.S. Pat. No. 5,891,689 entitled "Heme-bearing microparticles for targeted delivery of drugs"; U.S. Pat. No. 5,883,223 entitled "CD9 antigen peptides and antibodies thereto"; U.S. Pat. No. 5,877,022 entitled "Ribozymes targeted to APO(a) RNA"; U.S. Pat. No. 5,874,250 entitled "DNA encoding for a protein containing the extracellular domain of lymphocyte activation gene 3"; U.S. Pat. No. 5,441,868 entitled "Production of recombinant erythropoietin"; U.S. Pat. No. 5,869,445 entitled "Methods for eliciting or enhancing reactivity to HER-2/neu protein"; U.S. Pat. No. 5,030,621 entitled "Shed melanoma antigen compositions"; U.S. Pat. No. 5,859,309 entitled "Vector for integration site independent gene expression in mammalian host cells"; U.S. Pat. No. 5,075,213 entitled "Method for detection and prevention of human cytomegalovirus infection"; and in publications: Das et al., "Upstream regulatory elements are necessary and sufficient for transcription of a U6 RNA gene by RNA polymerase III" EMBO J. (1988) 7:503–512.; Kunkel et al., "U6 small nuclear RNA is transcribed by RNA polymerase III" Proc. Natl. Acad. USA (1986) 83:8575–8579.; Murphy et al., "The in vitro transcription of the 7SK RNA gene by RNA polymerase III is dependent only on the presence of an upstream promoter" Cell (1987) 51:81–87; Lichtenstein et al., "Effects of .beta.-2 Microglobulin Anti-sense oligonucleotides on Sensitivity of HER2/neu Oncogene-Expressing and Nonexpressing Target Cells to Lymphocyte-Mediated Lysis," Cellular Immunology 141:219–232, 1992; Keiffer et al., "Uncoupling in the Expression of Platelet GP IIb/IIIa in Human Endothelial Cells and K562 Cells: Absence of Immunologic Crossreactivity Between Platelet GP IIb and the Vitronectin Receptor Alpha Chain," Blood, 72(4): 1209–1215 (October, 1988); Moore, G. E. et al., American Medical Association 199: 519 (1967); these patents and documents are hereby incorporated by reference, as if set forth in their entirety herein.

Patents which may contain examples of gene delivery systems, that may possibly be used with at least one emodiment of the present invention may be found in U.S. Patent. Nos.: U.S. Pat. No. 5,853,663, issued to Wittig, et al on Dec. 29, 1998, and entitled "Pressure Distributor and Multi-Macrocarrier Assembly for Ballistic Transfer Transfection Apparatus; and U.S. Pat. No. 5,584,807, issued to McCabe on Dec. 17, 1996, and entitled Gas Driven Gene Delivery Instrument"; and are hereby incorporated by reference as if set forth in their entirety herein.

Examples of promoters and polyadenylation signals, or references providing same, which might possibly be useful to practice the present invention may be found in U.S. Pat. No. 5,593,972, issued on Jan. 14, 1997 to Weiner, et al; which patent and references are incorporated herein by references, as if set forth in their entirety herein.

For examples of silane reagents, modified bases and/or related materials and/or methodology which might possibly be used in at least one emobodiment of the present invention might be found in U.S. Patent Nos.: U.S. Pat. No. 5,286,878 entitled "Catalytic reduction of organic carbonyls"; U.S. Pat. No. 4,959,340 entitled "Method of making liquid chromatography packing materials"; U.S. Pat. No. 4,835,269 entitled "Silane reagents containing a complexion group"; U.S. Pat. No. 5,869,724, entitled, Asymmetric bidentate silanes; U.S. Pat. No. 5,879,938, entitled "Base-modified enzymatic nucleic acid; U.S. Pat. No. 5,780,300, entitled "Manipulation of non-terminally differentiated cells using the notch pathway"; U.S. Pat. No. 5,767,263, entitled "Base-modified enzymatic nucleic acid"; U.S. Pat. No. 5,750,103, entitled "Method for transplanting cells into the brain and therapeutic uses therefor"; U.S. Pat. No. 5,602,240, entitled "Backbone modified oligonucleotide analogs"; U.S. Pat. No. 5,631,359, entitled "Hairpin ribozymes"; and U.S. Pat. No. 5,610,289, entitled "Backbone modified oligonucleotide analogues"; which are incorporated by reference, as if set forth in their entirety herein.

For illustrative methodology relating to molecular biology techniques, U.S. Pat. No. 5,866,551 is incorporated herein by reference. These techniques include, for example, the preparative extractions of plasmid DNA, centrifugation of plasmid DNA in caesium chloride gradient, agarose or acrylamide gel electrophoresis, purification of DNA fragments by electroelution, phenol or phenol-chloroform extraction of proteins, transformation in *Escherichia coli*, precipitation of DNA in saline medium, for example, see Maniatis, T., et al., "Molecular Cloning, a Laboratory Manual," Cold Spring Harbor Laboratory, Cold Spring Harbor, N.Y. 1982; Ausubel F. M., et al.(eds.), "Current Protocols in Molecular Biology," John Wiley & Sons, NY, 1987. For illustrative methodology relating to the enzymatic amplification of DNA fragments by the PCR technique, see Polymerase-catalyzed Chain Reaction, Saiki R. K. et al., Science 230(1985) 1350–1354; Mullis K. B. and Faloona F. A., Meth Enzym. 155 (1987) 335–350. For illustrative methodology relating to verification of nucleotide sequences, see, Proc. Natl. Sci. USA, 74 (1977) 5463–5467 (method developed by Sanger et al., using kit distributed by Amersham). Sanger et al. For illustrative methodology relating to ligations, DNA fragments can be separated according to size by agarose or acrylamide gel electrophoresis, extracted with phenol or with a phenol/chloroform mixture, precipitated with ethanol and then incubated in the presence of phage T4 DNA ligase (Biolabs) according to the instructions of the supplier. U.S. Pat. No. 5,866,551, and the above referenced treatises and documents which are hereby incorporated by reference, as if set forth in their entirety herein.

For illustrative methodology relating to DNA cloning or amplification, see, U.S. Pat. No. 5,683,909, entitled "Plasmids replicatable in Bacillus subtilis, e.coli and lactic acid streptococcus bacteria"; U.S. Pat. No. 5,376,527, entitled "Process for lysing mycobacteria"; U.S. Pat. No. 5,830,705, entitled "Method for recombinant production of human pluripotent granulocye colony-stimulating factor"; U.S. Pat. No. 5,621,080, entitled "Production of erythropoietin"; and U.S. Pat. No. 4,460,689, entitled "Cloning Vector TG1, derivative, and processes of making"; which are hereby incorporated by reference, as if set forth in their entirety herein.

Examples of tissue glue which might possibly be utilized with the present invention may be found in U.S. Patent Nos.: U.S. Pat. No. 5,824,015, entitled "Method for Welding Biological Tissue"; U.S. Pat. No. 5,773,418, entitled "Fibrin sealant compositions and methods for utilizing same"; U.S. Pat. No. 5,552,452, entitled "Organic tissue glue for closure of wounds"; and which are hereby incorporated by reference, as if set forth in their entirety herein.

Examples of genetic vaccination methods, procedures, materials, and/or apparatus, which might possibly be used in conjunction with at least one embodiment of the present invention may be found in the following U.S. Patents, which U.S. patents may also contain the full-names of abbreviations found herein, namely, U.S. Patent Nos: U.S. Pat. No. 5,889,038, entitled "Methods and products for treating diarrhea and scours: use of clotrimazole and related aromatic compounds"; U.S. Pat. No. 5,880,103, entitled "Immunomodulatory peptides"; U.S. Pat. No. 5,869,058, entitled "Peptides used as carriers in immunogenic constructs suitable for development of synthetic vaccines"; U.S. Pat. No. 5,866,553, entitled "Polynucleotide vaccine for papillomavirus"; U.S. Pat. No. 5,861,397, entitled "Piperazine based cytofectins"; U.S. Pat. No. 5,861,290, entitled "Methods and polynucleotide constructs for treating host cells for infection or hyperproliferative disorders"; U.S. Pat. No. 5,859,324, entitled "Hypersensitive response induced resistance in plants"; U.S. Pat. No. 5,846,961, entitled "Multi-faceted method to repress reproduction of latent viruses in humans and animals"; U.S. Pat. No. 5,840,707 entitled "Stabilizing and delivery means of biological molecules"; U.S. Pat. No. 5,837,511, entitled "Non-group C adenoviral vectors"; U.S.

Pat. No. 5,837,510, entitled "Methods and polynucleotide constructs for treating host cells for infection or hyperproliferative disorders"; U.S. Pat. No. 5,837,269, entitled "Vaccine compositions and method for enhancing an immune response"; U.S. Pat. No. 5,830,876, entitled "Genetic immunization"; U.S. Pat. No. 5,824,313, entitled "Vaccine compositions and method for induction of mucosal immune response via systemic vaccination"; U.S. Pat. No. 5,817,637, entitled "Genetic immunization"; U.S. Pat. No. 5,780,448, entitled "DNA-based vaccination of fish"; U.S. Pat. No. 5,776,889, entitled "Hypersensitive response induced resistance in plants"; U.S. Pat. No. 5,738,852, entitled "Methods of enhancing antigen-specific T cell responses"; U.S. Pat. No. 5,736,524, entitled "Polynucleotide tuberculosis vaccine"; U.S. Pat. No. 5,891,432, entitled "Membrane-bound cytokine compositions comprising GM=CSF and methods of modulating an immune response using same"; U.S. Pat. No. 5,889,156, entitled "TNF deletion muteins"; U.S. Pat. No. 5,888,814, entitled "Recombinant host cells encoding TNF proteins"; U.S. Pat. No. 5,888,502, entitled "Recombinant retroviruses"; U.S. Pat. No. 5,882,640, entitled "Treatment of hyperallergenic response with oral interferon"; U.S. Pat. No. 5,879,675, entitled "Compositions and methods for vaccines comprising .alpha.-galactosyl epitopes"; U.S. Pat. No. 5,874,077, entitled "Human til cells expressing recombinant TNF prohormone"; U.S. Pat. No. 5,861,164, entitled "Vaccination against diseases resulting from pathogenic responses by specific T cell populations"; U.S. Pat. No. 5,853,765, entitled "Anti-cholesterolemic egg, vaccine and method for production, and use"; U.S. Pat. No. 5,849,586, entitled "Infective protein delivery system"; U.S. Pat. No. 5,846,526, entitled "Treatment of autoimmune disorders with oral interferon"; U.S. Pat. No. 5,837,246, entitled "Vaccination and methods against diseases resulting from pathogenic responses by specific T cell populations"; U.S. Pat. No. 5,830,458, entitled "Method for destroying a diseased human cell"; U.S. Pat. No. 5,830,456, entitled "Treatment of viral disease with oral interferon-.alpha."; U.S. Pat. No. 5,824,300, entitled "Treatment of neoplastic disease with oral interferon"; U.S. Pat. No. 5,817,307, entitled "Treatment of bacterial infection with oral interferon-.alpha."; U.S. Pat. No. 5,804,191, entitled "Sperm as immunogen carriers"; U.S. Pat. No. 5,804,187, entitled "Modified antibodies with human milk fat globule specificity"; U.S. Pat. No. 5,780,304, entitled "Diagnosis and treatment of insulin dependent diabetes mellitus using heat shock protein determinents"; U.S. Pat. No. 5,776,459, entitled "TCR V beta 5 peptides"; U.S. Pat. No. 5,766,625, entitled "Artificial viral envelopes"; U.S. Pat. No. 5,759,535, entitled "Immunotherapeutic strategies for the treatment of cancer"; U.S. Pat. No. 5,753,262, entitled "Cationic lipid acid salt of 3beta[N-(N',N'-dimethylaminoethane)-carbamoyl]cholesterol and halogenated solvent-free preliposomal lyophilate thereof"; U.S. Pat. No. 5,753,258, entitled "Artificial viral envelopes"; U.S. Pat. No. 5,736,139, entitled "Treatment of Clostridium difficile induced disease"; U.S. Pat. No. 5,728,385, entitled "Method and composition for an early vaccine to protect against both common infectious diseases and chronic immune mediated disorders or their sequelae"; U.S. Pat. No. 5,723,283, entitled "Method and composition for an early vaccine to protect against both common infectious diseases and chronic immune mediated disorders or their sequelae"; and these patents are hereby incorporated by reference, as if set forth in their entirety herein.

Examples of gene therapy methods, procedures, materials and/or apparatus, which might possibly be used in conjunction with at least one embodiment of the present invention may be found in the following U.S. Patents, which U.S. patents may also contain the full-names of abbreviations found herein, namely, U.S. Patent Nos: U.S. Pat. No. 5,891,857, entitled "Characterized BRCA1 and BRCA2 proteins and screening and therapeutic methods based on characterized BRCA1 and BRCA2 proteins"; U.S. Pat. No. 5,889,156, entitled "TNF deletion muteins"; U.S. Pat. No. 5,888,814, entitled "Recombinant host cells encoding TNF proteins"; U.S. Pat. No. 5,888,502, entitled "Recombinant retroviruses"; U.S. Pat. No. 5,888,498, entitled "Cellular and animal models for diseases associated with mitochondrial defects"; U.S. Pat. No. 5,885,971, entitled "Gene therapy by secretory gland expression"; U.S. Pat. No. 5,880,267, entitled "Trophinin and trophinin-assisting protein agonists, antibodies and antagonists"; U.S. Pat. No. 5,877,161, entitled "Cyclin D1 negative regulatory activity"; U.S. Pat. No. 5,876,923, entitled "Herpes simplex virus ICP4 as an inhibitor of apoptosis"; U.S. Pat. No. 5,876,712, entitled "Immune reactivity to HER-2/neu protein for diagnosis and treatment of malignancies in which the HER-2/neu oncogene is associated"; U.S. Pat. No. 5,874,077, entitled "Human til cells expressing recombinant TNF prohormone"; U.S. Pat. No. 5,872,154, entitled "Method of reducing an immune response to a recombinant adenovirus"; U.S. Pat. No. 5,871,733, entitled "Multimeric forms of human rhinovirus receptor protein"; U.S. Pat. No. 5,871,732, entitled "Anti-CD4 antibody homologs useful in prophylaxis and treatment of AIDS, ARC and HIV infection"; U.S. Pat. No. 5,861,290, entitled "Methods and polynucleotide constructs for treating host cells for infection or hyperproliferative disorders"; U.S. Pat. No. 5,858,976, entitled "Methods for inhibiting interaction of human MDM2 and p53"; U.S. Pat. No. 5,858,784, entitled "Expression of cloned genes in the lung by aerosol-and liposome-based delivery"; U.S. Pat. No. 5,858,360, entitled "Trophinin and trophinin-assisting proteins"; U.S. Pat. No. 5,851,991, entitled "Therapeutic use of the retinoblastoma susceptibility gene product"; U.S. Pat. No. 5,851,833, entitled "Neomorphogenesis of urological structures in vivo from cell culture"; U.S. Pat. No. 5,849,586, entitled "Infective protein delivery system"; U.S. Pat. No. 5,846,538, entitled "Immune reactivity to HER-2/neu protein for diagnosis and treatment of malignancies in which the her-2/neu oncogene is associated"; U.S. Pat. No. 5,844,107, entitled "Compacted nucleic acids and their delivery to cells"; U.S. Pat. No. 5,843,432, entitled "Retroviral vectors for the treatment of tumors, and cell lines containing them"; U.S. Pat. No. 5,837,693, entitled "Intravenous hormone polypeptide delivery by salivary gland expression"; U.S. Pat. No. 5,837,510, entitled "Methods and polynucleotide constructs for treating host cells for infection or hyperproliferative disorders"; U.S. Pat. No. 5,834,591, entitled "Polypeptides and antibodies useful for the diagnosis and treatment of pathogenic neisseria and other microorganisms having type 4 pilin"; U.S. Pat. No. 5,831,031, entitled "Antibodies that bind to .alpha.2-antiplasmin crosslinked to fibrin which do not inhibit plasma .alpha.2antiplasmin"; U.S. Pat. No. 5,830,876, entitled "Genetic immunization"; U.S. Pat. No. 5,830,463, entitled "Yeast-based delivery vehicles"; U.S. Pat. No. 5,830,458, entitled "Method for destroying a diseased human cell"; U.S. Pat. No. 5,827,703, entitled "Methods and composition for in vivo gene therapy"; U.S. Pat. No. 5,827,686, entitled "Method of expressing genes in mammalian cells"; U.S. Pat. No. 5,824,642, entitled "Treatment of partial growth hormone insensitivity syndrome"; U.S. Pat. No. 5,817,637, entitled "Genetic immunization"; U.S. Pat. No. 5,817,491, entitled "VSV G pseusdotyped retroviral vectors"; U.S. Pat. No. 5,814,647, entitled "Use of troglitazone and related compounds for the treatment of the climacteric symptoms"; U.S. Pat. No. 5,804,191, entitled "Sperm as immunogen carriers"; U.S. Pat. No. 5,804,178, entitled "Implantation of cell-matrix structure adjacent mesentery, omentum or peritoneum tissue"; U.S. Pat. No. 5,795,967, entitled "Tumor necrosis factor antagonists and their use"; U.S. Pat. No. 5,795,872, entitled "DNA construct for immunization"; U.S. Pat. No. 5,792,751, entitled "Tranformation of cells associated with fluid spaces"; U.S. Pat. No. 5,792,645, entitled "Protein-polycation nucleic acid complexes and methods of use"; U.S. Pat. No. 5,792,453, entitled "Gene transfer-mediated angiogenesis therapy"; U.S. Pat. No. 5,786,341, entitled "Use of a COL1A1 mini-gene construct to inhibit collagen synthesis"; U.S. Pat. No. 5,786,213, entitled "Inhibition of endogenous gastrin expression for treatment of colorectal cancer"; U.S. Pat. No. 5,785,964, entitled "Three-dimensional genetically engineered cell and tissue culture system"; U.S. Pat. No. 5,780,448, entitled "DNA-based vaccination of fish"; U.S. Pat. No. 5,776,891, entitled "Compositions for reducing multidrug resistance"; U.S. Pat. No. 5,770,580, entitled "Somatic gene therapy to cells associated with fluid spaces"; U.S. Pat. No. 5,770,429, entitled "Transgenic non-human animals capable of producing heterologous antibodies"; U.S. Pat. No. 5,766,901, entitled "Apparatus and method for delivering a nucleotide into cell nuclei"; U.S. Pat. No. 5,763,416, entitled "Gene transfer into bone cells and tissues"; U.S. Pat. No. 5,762,926, entitled "Method of grafting genetically modified cells to treat defects, disease or damage of the central nervous system"; U.S. Pat. No. 5,759,517, entitled "Hemoglobins as drug delivery agents"; U.S. Pat. No. 5,756,466, entitled "Inhibitors of interleukin-1.beta. converting enzyme"; U.S. Pat. No. 5,756,455, entitled "Amplification of human MDM2 gene in human tumors"; U.S. Pat. No. 5,756,353, entitled "Expression of cloned genes in the lung by aerosol- and liposome-based delivery"; U.S. Pat. No. 5,756,264, entitled "Expression vector systems and method of use"; U.S. Pat. No. 5,753,441, entitled "170-linked breast and ovarian cancer susceptibility gene"; U.S. Pat. No. 5,750,106, entitled "Human monoclonal antibodies to cytomegalovirus"; U.S. Pat. No. 5,750,103, entitled "Method for transplanting cells into the brain and therapeutic uses therefor"; U.S. Pat. No. 5,747,469, entitled "Methods and compositions comprising DNA damaging agents and p53"; U.S. Pat. No. 5,744,139, entitled "Insulin-like growth factor I(IGF-1) induced improvement of depressed T4/T8 ratios"; U.S. Pat. No. 5,741,685, entitled "Parenchymal cells packaged in immunoprotective tissue for implantation"; U.S. Pat. No. 5,739,118, entitled "Compositions and methods for delivery of genetic material"; U.S. Pat. No. 5,733,543, entitled "Introduction of HIV-protective genes into cells by particle-mediated gene transfer"; U.S. Pat. No. 5,716,929, entitled "Inhibitors of interleukin-1.beta. converting enzyme"; and U.S. Pat. No. 5,709,854, entitled "Tissue formation by injecting a cell-polymeric solution that gels in vivo"; and these patents are hereby incorporated by reference, as if set forth in their entirety herein.

International publication numbers WO 96 32473 A, published Oct. 17, 1996; European Patent No. EP 0 686 697 A (Soft Gene, GmbH), published Dec. 13, 1995; French Patent No. FR 2732971 A, published Oct. 18, 1996; European Patent No. 0820508 A, published Jan. 28, 1998; and German Patent No. DE 4416784 A, published Nov. 30, 1995; C. Clusel,et al. Nucleic Acids Research, vol 21, no. 15, Juillet 1993, Oxford GB, 3405-3411, XP002005499, "Ex Vivo Regulation of Specific Gene Gene Expression by Nanomolar Concentration of Double-Stranded Dumbbell Oligonucleotides" cit' dans la demande voir le document en entier; B. C. F. Chu et al., Nucleic Acids Research, vol 20, no. 21, Nov. 11, 1992, Oxford GB, 5857–5858, XP002005500, "The Stabilitu of Different Forms of Double-Stranded Decoy DNA in Serum and Nuclear Extracts" cit' dans la demande voir le document en entier; are each hereby incorporated by reference, as if set out in their entirety herein.

Reference books which may contain further explanations of abreviations and/or methods referenced herein may be found in the following documents: Gale Encyclopedia of Medicine vol. 3, publisher—Gale Research 1999; Health Reference Series vol. 13—Genetic Disorders Source Book, publisher—Frederick G. Ruffner, Jr., Pub. 1996; Encyclopedia of Molecular Biology and Molecular Medicine, editor—Robert A. Meyers, publisher—VCH Publishers New York 1996, 6 volumes; Dictionary of Gene Technology, editor—Gunther Kahl, publisher—VCH Publishers, New York 1995; Dictionary of Genetics, 5th edition, editor—Robert C. King, publisher—Oxford University Press, New York 1997; Encyclopedia of Human Biology, editor—R. Dulbecco, publisher—Academic Press , New York 1997, 9 volumes; and Biology, E. Solomon, L. Berg, D. Martin and C. Villee, publisher—Saunders College Publishing, Harcourt Brace College Publishers, 1993; which books are hereby incorporated by reference as if set forth in their entirety herein.

Some of the materials which may be needed to perform some of the procedures described herein, for example, gene lines, plasmids, cloning vectors, cell culture media, DNA, reagents, etc., can be obtained from American Type Culture Collection (ATCC), 10801 University Blvd., Manassas, Va., 20110–2204; Bio-Lab LTD, Industrial Area Atarot, P.O.B. 34038, Jerusalem 91340, Israel; International Biotechnologies Inc., Newhaven, Conn. 06535 and/or Molecular Biology Institute (MBI), La Jolla, Calif. 92037.

All of the patents, patent applications and publications recited herein, and in the Declaration attached hereto, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The invention as described hereinabove in the context of the preferred embodiments is not to be taken as limited to all of the provided details thereof, since modifications and variations thereof may be made without departing from the spirit and scope of the invention.

It is hereby noted that the prefix or word desoxy can be a form of the prefix or word "deoxy."

It is hereby noted that on page 15, line 27, "erytroleukemia cell line K562" may be referring to erythroleukemia cell line K562."

SEQUENCE LISTING

<160> NUMBER OF SEQ ID NOS: 13

<210> SEQ ID NO 1
<211> LENGTH: 1078
<212> TYPE: DNA
<213> ORGANISM: Artificial Sequence
<220> FEATURE:
<221> NAME/KEY: gene
<222> LOCATION: (1)..(1078)
<223> OTHER INFORMATION: bcr3=abl2; Oligo DNA Dumbbell
<220> FEATURE:
<221> NAME/KEY: misc_binding
<222> LOCATION: (1)..(2)
<223> OTHER INFORMATION: intramolecular binding site; the T-nucleotides
at position 1 to 2 can be modified with amino or caroxy features
<220> FEATURE:
<221> NAME/KEY: misc_binding
<222> LOCATION: (1077)..(1078)
<223> OTHER INFORMATION: intramolecular binding site; the T-nucleotides
at position 1077 to 1078 can be modified with amino or caroxy
features
<220> FEATURE:
<223> OTHER INFORMATION: Description of Artificial Sequence: Strandness:
both; nucleic acid (linear), hypothetical: No, anti-sense: No

<400> SEQUENCE: 1

```
ttcggccggc caagcttaac cgtattaccg ccatgcatta gttattaata gtaatcaatt      60
acggggtcat tagttcatag cccatatatg gagttccgcg ttacataact tacggtaaat     120
ggcccgcctg gctgaccgcc caacgacccc cgcccattga cgtcaataat gacgtatgtt     180
cccatagtaa cgccaatagg gactttccat tgacgtcaat gggtggagta tttacggtaa     240
actgcccact tggcagtaca tcaagtgtat catatgccaa gtacgccccc tattgacgtc     300
aatgacggta aatggcccgc ctggcattat gcccagtaca tgaccttatg gactttcct     360
acttggcagt acatctacgt attagtcatc gctattacca tggtgatgcg gttttggcag     420
tacatcaatg ggcgtggata gcggtttgac tcacggggat ttccaagtct ccacccatt     480
gacgtcaatg ggagtttgtt ttggcaccaa aatcaacggg actttccaaa atgtcgtaac     540
aactccgccc cattgacgca aatgggcggt aggcgtgtac ggtgggaggt ctatataagc     600
agagctggtt tagtgaaccg tcagatggta ccatgctgac caactcgtgt gtgaaactcc     660
agactgtcca cagcattccg ctgaccatca ataaggaaga tgatgagtct ccggggctct     720
atgggtttct gaatgtcatc gtccactcag ccactggatt taagcagagt tcaaaagccc     780
ttcagcggcc agtagcatct gactttgagc ctcagggtct gagttaagag ctcataatca     840
gccataccac atttgtagag gttttacttg ctttaaaaaa cctcccacac ctcccctga     900
acctgaaaca taaatgaat gcaattgttg ttgttaactt gtttattgca gcttataatg     960
gttacaaata aagcaatagc atcacaaatt tcacaaataa agcatttttt tcactgcatt    1020
ctagttgtgg tttgtccaaa ctcatcaatg tatcttaacg cgaattcggc cggccgtt     1078
```

<210> SEQ ID NO 2
<211> LENGTH: 1645
<212> TYPE: DNA
<213> ORGANISM: Artificial Sequence
<220> FEATURE:
<221> NAME/KEY: gene
<222> LOCATION: (1)..(1645)
<223> OTHER INFORMATION: Interleukin-12 (IL-12, p35-subunit); Oligo DNA
Dumbbell
<220> FEATURE:
<221> NAME/KEY: misc_binding
<222> LOCATION: (1)..(2)

```
<223> OTHER INFORMATION: intramolecular binding site; the T-nucleotides
      at position 1 to 2  can be modified with amino or carox features
<220> FEATURE:
<221> NAME/KEY: misc_binding
<222> LOCATION: (1644)..(1645)
<223> OTHER INFORMATION: intramolecular binding site; the T-nucleotides
      at position 1644 to 1645  can be modified with amino or caroxy
      features
<220> FEATURE:
<223> OTHER INFORMATION: Description of Artificial Sequence:
      Strandness: both;  nucleic acid (linear), hypothetical: No,
      anti-sense: No

<400> SEQUENCE: 2
ttcggccggc caagcttaac cgtattaccg ccatgcatta gttattaata gtaatcaatt     60
acggggtcat tagttcatag cccatatatg gagttccgcg ttacataact tacggtaaat    120
ggcccgcctg gctgaccgcc caacgacccc cgcccattga cgtcaataat gacgtatgtt    180
cccatagtaa cgccaatagg gactttccat tgacgtcaat gggtggagta tttacgtaa     240 actgcccact tggcagtaca tcaagtgtat catatgccaa gtacgccccc tattgacgtc    300
aatgacggta atggcccgc  ctggcattat gcccagtaca tgaccttatg ggactttcct    360
acttggcagt acatctacgt attagtcatc gctattacca tggtgatgcg gttttggcag    420
tacatcaatg ggcgtggata gcggtttgac tcacggggat ttccaagtct ccaccccatt    480
gacgtcaatg ggagtttgtt ttggcaccaa atcaacggg  actttccaaa atgtcgtaac    540
aactccgccc cattgacgca aatgggcggt aggcgtgtac ggtgggaggt ctatataagc    600
agagctggtt tagtgaaccg tcagatggta ccatgtggcc cctgggtca  gcctcccagc    660 caccgccctc acctgccgcg gccacaggtc tgcatccagc ggctcgccct gtgtccctgc    720
agtgccggct cagcatgtgt ccagcgcgca gcctcctcct tgtcgctacc ctggtcctcc    780
tggaccacct cagtttggcc agaaacctcc ccgtggccac tccagaccca ggaatgttcc    840
catgccttca ccactcccaa aacctgctga gggccgtcag caacatgctc cagaaggcca    900
gacaaactct agaattttac ccttgcactt ctgaagagat tgatcatgaa gatatcacaa    960
aagataaaac cagcacagtg gaggcctgtt taccattgga attaaccaag aatgagagtt   1020
gcctaaattc cagagagacc tctttcataa ctaatgggag ttgcctggcc tccagaaaga   1080 cctctttat  gatggccctg tgccttagta gtatttatga agacttgaag atgtaccagg   1140
tggagttcaa gaccatgaat gcaaaacttc tgatggatcc taagaggcag atctttctag   1200
atcaaaacat gctggcagtt attgatgagc tgatgcaggc cctgaatttc aacagtgaga   1260
ctgtgccaca aaaatcctcc cttgaagaac cggatttta taaaactaaa atcaagctct   1320
gcatacttct tcatgctttc agaattcggg cagtgactat tgatagagtg atgagctatc   1380
tgaatgcttc ctaagagctc ataatcagcc ataccacatt tgtagaggtt ttacttgctt   1440
taaaaaacct cccacacctc cccctgaacc tgaaacataa aatgaatgca attgttgttg   1500
ttaacttgtt tattgcagct tataatggtt acaaataaag caatagcatc acaaatttca   1560
caaataaagc attttttca  ctgcattcta gttgtggttt gtccaaactc atcaatgtat   1620
cttaacgcga attcggccgg ccgtt                                         1645
```

<210> SEQ ID NO 3
<211> LENGTH: 1318
<212> TYPE: DNA
<213> ORGANISM: Artificial Sequence
<220> FEATURE:
<221> NAME/KEY: gene
<222> LOCATION: (1)..(1318)

<223> OTHER INFORMATION: GM-CSF; Oligo DNA Dumbbell
<220> FEATURE:
<221> NAME/KEY: misc_binding
<222> LOCATION: (1)..(2)
<223> OTHER INFORMATION: intramolecular binding site; the T-nucleotides
at position 1 to 2 can be modified with amino or carboxy features
<220> FEATURE:
<221> NAME/KEY: misc_binding
<222> LOCATION: (1317)..(1318)
<223> OTHER INFORMATION: intramolecular binding site; the T-nucleotides
at position 1317 to 1318 can be modified with amino or caroxy
features
<220> FEATURE:
<223> OTHER INFORMATION: Description of Artificial Sequence:
Strandness: both; nucleic acid (linear), hypothetical: No,
anti-sense: No

<400> SEQUENCE: 3

```
ttcggccggc caagcttaac cgtattaccg ccatgcatta gttattaata gtaatcaatt      60
acggggtcat tagttcatag cccatatatg gagttccgcg ttacataact tacggtaaat     120
ggcccgcctg gctgaccgcc caacgacccc cgcccattga cgtcaataat gacgtatgtt     180
cccatagtaa cgccaatagg gactttccat tgacgtcaat gggtggagta tttacgtaa      240
actgcccact tggcagtaca tcaagtgtat catatgccaa gtacgccccc tattgacgtc     300
aatgacggta atggcccgc ctggcattat gcccagtaca tgaccttatg gactttcct      360
acttggcagt acatctacgt attagtcatc gctattacca tggtgatgcg gttttggcag     420
tacatcaatg ggcgtggata gcggtttgac tcacggggat ttccaagtct ccaccccatt     480
gacgtcaatg ggagtttgtt ttggcaccaa atcaacggg actttccaaa atgtcgtaac      540
aactccgccc cattgacgca aatgggcggt aggcgtgtac ggtgggaggt ctatataagc     600
agagctggtt tagtgaaccg tcagatggta ccatgtggct gcagagcctg ctgctcttgg     660
gcactgtggc ctgcagcatc tctgcacccg cccgctcgcc cagccccagc acacagccct     720
gggagcatgt gaatgccatc caggaggccc ggcgtctcct gaacctgagt agagacactg     780
ctgctgagat gaatgaaaca gtagaagtca tctcagaaat gtttgacctc caggagccga     840
cctgcctaca gacccgcctg gagctgtaca gcagggcct gcggggcagc ctcaccaagc      900
tcaagggccc cttgaccatg atggccagcc actacaaaca gcactgccct caaccccgg      960
aaacttcctg tgcaacccag attatcacct ttgaaagttt caagagaac ctgaaggact     1020
ttctgcttgt catccccttt gactgctggg agccagtcca ggagtgagag ctcataatca     1080
gccataccac atttgtagag gttttacttg ctttaaaaaa cctcccacac ctcccctga     1140
acctgaaaca taaatgaat gcaattgttg ttgttaactt gttattca gcttataatg      1200
gttacaaata aagcaatagc atcacaaatt tcacaaataa agcattttt tcactgcatt     1260
ctagttgtgg tttgtccaaa ctcatcaatg tatcttaacg cgaattcggc cggccgtt      1318
```

<210> SEQ ID NO 4
<211> LENGTH: 1870
<212> TYPE: DNA
<213> ORGANISM: Artificial Sequence
<220> FEATURE:
<221> NAME/KEY: gene
<222> LOCATION: (1)..(1870)
<223> OTHER INFORMATION: Interleukin-12 (IL-12, p40-subunit); Oligo DNA
Dumbbell
<220> FEATURE:
<221> NAME/KEY: misc_binding
<222> LOCATION: (1)..(2)
<223> OTHER INFORMATION: intramolecular binding site; the T-nucleotides
at position 1 to 2 can be modified with amino or caroxy features
<220> FEATURE:

<221> NAME/KEY: misc_binding
<222> LOCATION: (1869)..(1870)
<223> OTHER INFORMATION: intramolecular binding site; the T-nucleotides at position 1869 to 1870 can be modified with amino or caroxy features
<220> FEATURE:
<223> OTHER INFORMATION: Description of Artificial Sequence: Strandness: both; nucleic acid (linear), hypothetical: No, anti-sense: No

<400> SEQUENCE: 4

```
ttcggccggc caagcttaac cgtattaccg ccatgcatta gttattaata gtaatcaatt     60
acggggtcat tagttcatag cccatatatg gagttccgcg ttacataact tacggtaaat    120
ggcccgcctg gctgaccgcc caacgacccc cgcccattga cgtcaataat gacgtatgtt    180
cccatagtaa cgccaatagg gactttccat tgacgtcaat gggtggagta tttacggtaa    240
actgcccact tggcagtaca tcaagtgtat catatgccaa gtacgccccc tattgacgtc    300
aatgacggta aatggcccgc ctggcattat gcccagtaca tgaccttatg ggactttcct    360
acttggcagt acatctacgt attagtcatc gctattacca tggtgatgcg gttttggcag    420
tacatcaatg ggcgtggata gcggtttgac tcacgggat ttccaagtct ccaccccatt    480
gacgtcaatg ggagtttgtt ttggcaccaa aatcaacggg actttccaaa atgtcgtaac    540
aactccgccc cattgacgca aatgggcggt aggcgtgtac ggtgggaggt ctatataagc    600
agagctggtt tagtgaaccg tcagatggta ccatgtgtca ccagcagttg gtcatctctt    660
ggttttccct ggttttttctg gcatctcccc tcgtggccat atgggaactg aagaaagatg    720
tttatgtcgt agaattggat tggtatccgg atgcccctgg agaaatggtg gtcctcacct    780
gtgacaccccc tgaagaagat ggtatcacct ggaccttgga ccagagcagt gaggtcttag    840
gctctggcaa aaccctgacc atccaagtca aagagtttgg agatgctggc cagtacacct    900
gtcacaaagg aggcgaggtt ctaagccatt cgctcctgct gcttcacaaa aaggaagatg    960
gaatttggtc cactgatatt ttaaaggacc agaaagaacc caaaaataag accttttctaa   1020
gatgcgaggc caagaattat tctggacgtt tcacctgctg gtggctgacg acaatcagta   1080
ctgatttgac attcagtgtc aaaagcagca gaggctcttc tgacccccaa ggggtgacgt   1140
gcggagctgc tacactctct gcagagagag tcagagggga caacaaggag tatgagtact   1200
cagtggagtg ccaggaggac agtgcctgcc cagctgctga ggagagtctg cccattgagg   1260
tcatggtgga tgccgttcac aagctcaagt atgaaaacta caccagcagc ttcttcatca   1320
gggacatcat caaacctgac ccacccaaca acttgcagct gaagccatta aagaattctc   1380
ggcaggtgga ggtcagctgg gagtaccctg acacctggag tactccacat tcctacttct   1440
ccctgacatt ctgcgttcag gtccagggca agagcaagag agaaaagaaa gatagagtct   1500
tcaccgacaa gacctcagcc acggtcatct gccgcaaaaa tgccagcatt agcgtgcggg   1560
cccaggaccg ctactatagc tcatcttgga gcgaatgggc atctgtgccc tgcagttagg   1620
agctcataat cagccatacc acatttgtag aggtttact tgctttaaaa aacctcccac   1680
acctccccct gaacctgaaa cataaaatga atgcaattgt tgttgttaac ttgtttattg   1740
cagcttataa tggttacaaa taaagcaata gcatcacaaa tttcacaaat aaagcatttt   1800
tttcactgca ttctagttgt ggtttgtcca aactcatcaa tgtatcttaa cgcgaattcg   1860
gccggccgtt                                                          1870
```

<210> SEQ ID NO 5
<211> LENGTH: 1417

```
<212> TYPE: DNA
<213> ORGANISM: Artificial Sequence
<220> FEATURE:
<221> NAME/KEY: gene
<222> LOCATION: (1)..(1417)
<223> OTHER INFORMATION: Interleukin-7 (IL-7); Oligo DNA Dumbbell
<220> FEATURE:
<221> NAME/KEY: misc_binding
<222> LOCATION: (1)..(2)
<223> OTHER INFORMATION: intramolecular binding site; the T-nucleotides
      at position 1 to 2 can be modified with amino or caroxy features
<220> FEATURE:
<221> NAME/KEY: misc_binding
<222> LOCATION: (1416)..(1417)
<223> OTHER INFORMATION: intramolecular binding site; the T-nucleotides
      at position 1416 to 1417 can be modified with amino or caroxy
      features
<220> FEATURE:
<223> OTHER INFORMATION: Description of Artificial Sequence:
      Strandness: both;  nucleic acid (linear),  hypothetical: No,
      anti-sense: No

<400> SEQUENCE: 5
ttcggccggc caagcttaac cgtattaccg ccatgcatta gttattaata gtaatcaatt      60
acggggtcat tagttcatag cccatatatg gagttccgcg ttacataact tacggtaaat    120
ggcccgcctg gctgaccgcc caacgacccc cgcccattga cgtcaataat gacgtatgtt    180
cccatagtaa cgccaatagg gactttccat tgacgtcaat gggtggagta tttacggtaa    240
actgcccact tggcagtaca tcaagtgtat catatgccaa gtacgccccc tattgacgtc    300
aatgacggta aatggcccgc ctggcattat gcccagtaca tgaccttatg gactttcct     360 acttggcagt acatctacgt attagtcatc gctattacca tggtgatgcg gttttggcag    420
tacatcaatg ggcgtggata gcggtttgac tcacggggat ttccaagtct ccaccccatt    480
gacgtcaatg ggagtttgtt ttggcaccaa atcaacggg  actttccaaa atgtcgtaac    540
aactccgccc cattgacgca aatgggcggt aggcgtgtac ggtgggaggt ctatataagc    600
agagctggtt tagtgaaccg tcagatggta ccatgttcca tgtttctttt aggtatatct    660
ttggacttcc tcccctgatc cttgttctgt tgccagtagc atcatctgat tgtgatattg    720
aaggtaaaga tggcaaacaa tatgagagtg ttctaatggt cagcatcgat caattattgg    780
acagcatgaa agaaattggt agcaattgcc tgaataatga atttaacttt ttaaaagac    840 atatctgtga tgctaataag gaaggtatgt ttttattccg tgctgctcgc aagttgaggc    900 aattcttaa aatgaatagc actggtgatt ttgatctcca cttattaaaa gtttcagaag    960
gcacaacaat actgttgaac tgcactggcc aggttaaagg aagaaaacca gctgccctgg   1020
gtgaagccca accaacaaag agtttggaag aaaataaatc tttaaaggaa cagaaaaaac   1080
tgaatgactt gtgtttccta agagactat tacaagagat aaaaacttgt tggaataaaa   1140
ttttgatggg cactaaagaa cactgagagc tcataatcag ccataccaca tttgtagagg   1200
ttttacttgc tttaaaaaac ctcccacacc tcccctgaa  cctgaaacat aaaatgaatg   1260
caattgttgt tgttaacttg tttattgcag cttataatgg ttacaaataa agcaatagca   1320
tcacaaattt cacaaataaa gcatttttt  cactgcattc tagttgtggt ttgtccaaac   1380
tcatcaatgt atcttaacgc gaattcggcc ggccgtt                            1417

<210> SEQ ID NO 6
<211> LENGTH: 28
<212> TYPE: DNA
<213> ORGANISM: Artificial Sequence
<220> FEATURE:
<221> NAME/KEY: misc_feature
```

```
<222> LOCATION: (1)..(28)
<223> OTHER INFORMATION: DNA; single strandness; topology: linear;
      "First oligonucleotide, description; example 1.2"
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 6
aattcggccg gccgttttcg gccggccg                                      28

<210> SEQ ID NO 7
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: DNA; single strandness; topology: linear;
      "Second oligonucleotide, description; example 1.2"
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 7
agcttggccg gccgttttcg gccggcca                                      28

<210> SEQ ID NO 8
<211> LENGTH: 27
<212> TYPE: DNA
<213> ORGANISM: Artificial Sequence
<220> FEATURE:
<221> NAME/KEY: misc_feature
<222> LOCATION: (16)..(17)
<223> OTHER INFORMATION: experimental DNA; single strandness; topology:
      linear; "First oligonucleotide, description; example 3"; X=Amino-
      Uracil with via X coupled peptide.
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 8
aattcggccg gccgtttcgg ccggccg                                       27

<210> SEQ ID NO 9
<211> LENGTH: 27
<212> TYPE: DNA
<213> ORGANISM: Artificial Sequence
<220> FEATURE:
<221> NAME/KEY: misc_feature
<222> LOCATION: (16)..(17)
<223> OTHER INFORMATION: experimental DNA; single strandness; topology:
      linear; "Second oligonucleotide, description; example 3"; X=Amino-
      Uracil with via X coupled peptide.
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 9
agcttggccg gccgtttcgg ccggcca                                       27

<210> SEQ ID NO 10
<211> LENGTH: 27
<212> TYPE: DNA
<213> ORGANISM: Artificial Sequence
<220> FEATURE:
<221> NAME/KEY: misc_feature
<222> LOCATION: (16)..(17)
```

-continued

```
<223> OTHER INFORMATION: experimental DNA; single strandness; topology:
      linear; "First oligonucleotide, description; example 4"; X=Thiol-
      Modifier C6 S-S.
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 10
aattcggccg gccgtttcgg ccggccg                                          27

<210> SEQ ID NO 11
<211> LENGTH: 27
<212> TYPE: DNA
<213> ORGANISM: Artificial Sequence
<220> FEATURE:
<221> NAME/KEY: misc_feature
<222> LOCATION: (16)..(17)
<223> OTHER INFORMATION: experimental DNA; single strandness; topology:
      linear; "Second oligonucleotide, description; example 4"; X=Thiol-
      Modifier C6 S-S.
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 11
agcttggccg gccgtttcgg ccggcca                                          27

<210> SEQ ID NO 12
<211> LENGTH: 27
<212> TYPE: DNA
<213> ORGANISM: Artificial Sequence
<220> FEATURE:
<221> NAME/KEY: misc_feature
<222> LOCATION: (16)..(17)
<223> OTHER INFORMATION: experimental DNA; single strandness; topology:
      linear; "First oligonucleotide, description; example 6"; Y=Carboxy
      acid modified thymidin desoxynucleotid.
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 12
aattcggccg gccgtttcgg ccggccg                                          27

<210> SEQ ID NO 13
<211> LENGTH: 27
<212> TYPE: DNA
<213> ORGANISM: Artificial Sequence
<220> FEATURE:
<221> NAME/KEY: misc_feature
<222> LOCATION: (16)..(17)
<223> OTHER INFORMATION: experimental DNA; single strandness; topology:
      linear; "Second oligonucleotide, description; example 6"; Y=
      Carboxy acid modified thymidin desoxynucleotid.
<220> FEATURE:
<223> OTHER INFORMATION: Description of Artificial Sequence: single
      strandness nucleic acid (linear), genomic DNA, hypothetical: No,
      anti-sense: No

<400> SEQUENCE: 13
agcttggccg gccgtttcgg ccggcca                                          27
```

What is claimed is:

1. A DNA construct for transcription of RNA molecules, said construct comprising a circular strand of DNA which forms a dumbbell, said circular strand comprising a first complementary sequence, a first non-complementary sequence, a second complementary sequence and a second non-complementary sequence, wherein said first and second complementary sequences pair to form a duplex in said dumbbell and said duplex comprises a) a promoter sequence, b) a coding sequence, and c) a polyadenylation sequence or other stabilizing sequence, and wherein said first and second non-complementary sequences form single-strand loops in said dumbbell.

2. The DNA construct according to claim 1, wherein said loops comprise three to seven nucleotides, and wherein one or several of said nucleotides are covalently modified by carboxy-, amine-, thiole or aldehyde functional groups.

3. The DNA construct according to claim 2, comprising a peptide, which directs the transport of said DNA construct across a cell's endosome or linked to one of said covalently modified nucleotides.

4. The DNA construct according to claim 1, wherein said promoter sequence comprises: a 7SK promoter or a CMV promoter.

5. The DNA construct according to claim 1 wherein said coding sequence encodes:

a) interleukin-7;

b) interleukin-12 or at least one of its constitutive subunits;

c) gm-csf;

d) p16 or p53 protein or fragments thereof; or e) peptide fragments of mutated ki-ras, mutated p53 or bcr-abl translocation product with a length of between 10 and 100 amino acids.

6. The DNA construct according to claim 2 wherein said coding sequence encodes:

a) interleukin-7;

b) interleukin-12 or at least one of its constitutive subunits;

c) gm-csf;

d) p16 or p53 protein or fragments thereof; or e) peptide fragments of mutated ki-ras, mutated p53 or bcr-abl translocation product with a length of between 10 and 100 amino acids.

7. The DNA construct according to claim 3 wherein the coding sequence encodes:

a) interleukin-7;

b) interleukin-12 or at least one of its constitutive subunits;

c) gm-csf;

d) p16 or p53 protein or fragments thereof; or e) peptide fragments of mutated ki-ras, mutated p53 or bcr-abl translocation product with a length of between 10 and 100 amino acids.

8. The DNA construct according to claim 4, wherein the coding sequence encodes:

a) interleukin-7;

b) interleukin-12 or at least one of its constitutive subunits;

c) gm-csf;

d) p16 or p53 protein or fragments thereof; or e) peptide fragments of mutated ki-ras, mutated p53 or bcr-abl translocation product with a length of between 10 and 100 amino acids.

9. A microprojectile for ballistic transfer into a cell, said microprojectile having a DNA construct linked thereto by adsorption, covalent binding or ionic binding, such that upon passage of said microprojectile through connective tissue, the DNA construct remains bound to said microprojectile until said DNA construct is in a target cell, wherein said DNA construct comprises a circular strand of DNA which forms a dumbbell, said circular strand comprising a first complementary sequence, a first non-complementary sequence, a second complementary sequence and a second non-complementary sequence, wherein said first and second complementary sequences pair to form a duplex in said dumbbell and said duplex comprises a) a promoter sequence, b) a coding sequence, and c) a polyadenylation sequence or other RNA-stabilizing sequence, and wherein said first and second non-complementary sequences form single-strand loops in said dumbbell.

10. A microparticle for ballistic transfer into a cell, said microprojectile having a DNA construct linked thereto by adsorption, covalent binding, or ionic binding, such that upon passage of said microprojectile through connective tissue, the DNA construct remains bound to said microprojectile until said DNA construct is in a target cell, wherein said DNA construct comprises a circular strand of DNA which forms a dumbbell, said circular strand comprising a first complementary sequence, a first non-complementary sequence, a second complementary sequence and a second non-complementary sequence, wherein said first and second complementary sequences pair to form a duplex in said dumbbell and said duplex comprises a) a promoter sequence, b) a coding sequence, and c) a polyadenylation sequence or other RNA-stabilizing stabilizing sequence, and wherein said first and second non-complementary sequences form single-strand loops in said dumbbell, wherein said promoter sequence comprises: a 7SK promoter or a CMV promoter, and wherein the coding sequence encodes:

a) interleukin-7;

b) interleukin-12 or at least one of its constitutive subunits;

c) gm-csf;

d) p16 or p53 protein or fragments thereof; or e) peptide fragments of mutated ki-ras, mutated p53 or bcr-abl translocation product with a length of between 10 and 100 amino acids.

11. A microprojectile for ballistic transfer of a DNA construct into cells, wherein the microprojectile comprises an attached DNA construct, and said DNA construct is selected from the group consisting of:

a) a circular strand of DNA which forms a dumbbell comprising a first complementary sequence, a first non-complementary sequence, a second complementary sequence, and a second non-complementary sequence, wherein first and second complementary sequences pair to form a duplex comprising a) a promoter sequence, b) a coding sequence, and c) a polyadenylation or other RNA sequence stabilizing sequence, and wherein first and second non-complementary sequences form single-strand loops;

b) a circular strand of DNA which forms a dumbbell comprising a first complementary sequence, a first non-complementary sequence, a second complementary sequence, and a second non-complementary sequence, wherein first and second complementary sequences pair to form a duplex comprising a) a promoter sequence, b) a coding sequence, and c) a polyadenylation sequence or other RNA stabilizing sequence; wherein first and second non-complementary sequences form single-strand loops comprising three to seven nucleotides of which one or several are covalently modified by carboxy-, amine-, thiole, or aldehyde functional groups;

c) a circular strand of DNA which forms a dumbbell comprising a first complementary sequence, a first non-complementary sequence, a second complementary sequence, and a second non-complementary sequence, wherein first and second complementary sequences pair to form a duplex comprising a) a promoter sequence, b) a coding sequence, and c) a polyadenylation sequence or other RNA stabilizing sequence, and wherein first and second non-complementary sequences form single-strand loops comprising three to seven nucleotides of which one or several are covalently modified by carboxy-, amine-, thiole, or aldehyde functional groups which in turn are linked to one or more peptides that direct DNA construct transport across a cell's endosome or into its nucleus.

d) a circular strand of DNA which forms a dumbbell comprising a first complementary sequence, a first non-complementary sequence, a second complementary sequence, and a second non-complementary sequence, wherein first and second complementary sequences pair to form a duplex comprising a) a promoter sequence comprising a 7SK promoter or a CMV promoter, b) a coding sequence, and c) a polyadenylation sequence or other RNA stabilizing sequence, and wherein first and second non-complementary sequences form single-strand loops;

e) a circular strand of DNA which forms a dumbbell comprising a first complementary sequence, a first non-complementary sequence, a second complementary sequence, and a second non-complementary sequence, wherein first and second complementary sequences pair to form a duplex comprising a promoter sequence operably linked to a coding sequence for interleukin-7, interleukin-12 or at least one of its constitutive subunits, gm-csf, p16 or p53 protein or fragments thereof, or peptide fragments of mutated ki-ras, mutated p53 or bcr-abl translocation product with a length of between 10 and 100 amino acids; a polyadenylation sequence or other RNA stabilizing sequence, and wherein first and second non-complementary sequences form single-strand loops;

f) a circular strand of DNA which forms a dumbbell comprising a first complementary sequence, a first non-complementary sequence, a second complementary sequence, and a second non-complementary sequence, wherein first and second complementary sequences pair to form a duplex comprising a promoter sequence, a coding sequence for interleukin-7, interleukin-12 or at least one of its constitutive subunits, gm-csf, p16 or p53 protein or fragments thereof, or peptide fragments of mutated ki-ras, mutated p53 or bcr-abl translocation product with a length of between 10 and 100 amino acids; a polyadenylation sequence or other RNA stabilizing sequence; and wherein first and second non-complementary sequences form single-strand loops comprising three to seven nucleotides, in which one or several of said nucleotides are covalently modified by carboxylic-, amine-, thiole or aldehyde functional groups;

g) a circular strand of DNA which forms a dumbbell comprising a first complementary sequence, a first non-complementary sequence, a second complementary sequence, and a second non-complementary sequence, wherein first and second complementary sequences pair to form a duplex comprising a promoter sequence, a coding sequence for interleukin-7, interleukin-12 or at least one of its constitutive subunits, gm-csf, p16 or p53 protein or fragments thereof, or peptide fragments of mutated ki-ras, mutated p53 or bcr-abl translocation product with a length of between 10 and 100 amino acids; a polyadenylation sequence or other RNA stabilizing sequence; and wherein first and second non-complementary sequences form single-strand loops comprising three to seven nucleotides, in which one or several of said nucleotides are covalently modified by carboxylic-, amine-, thiole or aldehyde functional groups which in turn are linked to one or more peptides that direct DNA construct transport across a cell's endosome or into its nucleus;

h) a circular strand of DNA which forms a dumbbell comprising a first complementary sequence, a first non-complementary sequence, a second complementary sequence, and a second non-complementary sequence, wherein first and second complementary sequences pair to form a duplex comprising a promoter sequence comprising a 7SK promoter or a CMV promoter, a coding sequence for interleukin-7, interleukin-12 or at least one of its constitutive subunits, gm-csf, p16 or p53 protein or fragments thereof, or peptide fragments of mutated ki-ras, mutated p53 or bcr-abl translocation product with a length of between 10 and 100 amino acids; a polyadenylation sequence sequence or other RNA stabilizing sequence; and wherein first and second non-complementary sequences form single-strand loops.

12. The microprojectile according to claim 9, wherein its material is gold, oxide ceramic, glass ceramic or glass; and said nucleic acid to be transported is bound covalently by thiole or disulfide moieties, ester-, amide-, aldimine-, ketale- or acetale- or ether functional groups to said microprojectile.

13. The microprojectile according to claim 10, wherein its material is gold, oxide ceramic, glass ceramic or glass; and said nucleic acid to be transported is bound covalently by thiole or disulfide moieties, ester-, amide-, aldimine-, ketale- or acetale- or ether functional groups to said microprojectile.

14. The microprojectile according to claim 11, wherein its material is gold, oxide ceramic, glass ceramic or glass; and said nucleic acid to be transported is bound covalently by thiole or disulfide moieties, ester-, amide-, aldimine-, ketale- or acetale- or ether functional groups to said microprojectile.

15. The microprojectile according to claim 9, wherein said microprojectile is made out of an electrically conductive material and said nucleic acid is linked to said microprojectile by electrochemically coupling of disulfide or thiole moieties, employing the microprojectile as an electrode.

16. The microprojectile according to claim 10, wherein said microprojectile is made out of an electrically conductive material and said nucleic acid is linked to said microprojectile by electrochemically coupling of disulfide or thiole moieties, employing the microprojectile as an electrode.

17. The microprojectile according to claim 11, wherein said microprojectile is made out of an electrically conductive material and said nucleic acid is linked to said microprojectile by electrochemically coupling of disulfide or thiole moieties, employing the microprojectile as an electrode.

18. The microprojectile according to claim 12, wherein said microprojectile is made out of an electrically conductive material and said nucleic acid is linked to said microprojectile by electrochemically coupling of disulfide or thiole moieties, employing the microprojectile as an electrode.

19. The microprojectile according to claim 13, wherein said microprojectile is made out of an electrically conductive material and said nucleic acid is linked to said microprojectile by electrochemically coupling of disulfide or thiole moieties, employing the microprojectile as an electrode.

20. The microprojectile according to claim 14, wherein said microprojectile is made out of an electrically conductive material and said nucleic acid is linked to said microprojectile by electrochemically coupling of disulfide or thiole moieties, employing the microprojectile as an electrode.

21. The microprojectile according to claim 9, wherein said microprojectile is of the size of 0.3 $\mu$m to 3 4 $\mu$m.

22. The microprojectile according to claim 10, wherein said microprojectile is of the size of 0.3 $\mu$m to 3 $\mu$m.

23. The microprojectile according to claim 11, wherein said microprojectile is of the size of 0.3 $\mu$m to 3 4 $\mu$m.

24. The microprojectile according to claim 12, wherein said microprojectile is of the size of 0.3 $\mu$m to 3 $\mu$m.

25. The microprojectile according to claim 13, wherein said microprojectile is of the size of 0.3 $\mu$m to 3 $\mu$m.

26. The microprojectile according to claim 14, wherein said microprojectile is of the size of 0.3 $\mu$m to 3 $\mu$m.

27. The microprojectile according to claim 15, wherein said microprojectile is of the size of 0.3 $\mu$m to 3 $\mu$m.

28. The microprojectile according to claim 16, wherein said microprojectile is of the size of 0.3 $\mu$m to 3 $\mu$m.

29. The microprojectile according to claim 17, wherein said microprojectile is of the size of 0.3 $\mu$m to 3 $\mu$m.

30. The microprojectile according to claim 18, wherein said microprojectile is of the size of 0.3 $\mu$m to 3 $\mu$m.

31. The microprojectile according to claim 19, wherein said microprojectile is of the size of 0.3 $\mu$m to 3 $\mu$m.

32. The microprojectile according to claim 20, wherein said microprojectile is of the size of 0.3 $\mu$m to 3 $\mu$m.

* * * * *

UNITED STATES PATENT AND TRADEMARK OFFICE
CERTIFICATE OF CORRECTION

PATENT NO.   : 6,451,593 B1
DATED        : September 17, 2002
INVENTOR(S)  : Burghardt Wittig and Class Junghans It is certified that error appears in the above-identified patent and that said Letters Patent is hereby corrected as shown below:

Column 21,
Before line 2, beginning with "<106>" insert the following:

```
--<110> Wittig, Prof. Burghardt
        Junghans, Claas
   <120> Design Principle for Constructing
         Expression Constructs for Gene
         Therapy
   <130> Xl 597/99
   <140> PCTDE97/02704
   <141> 1997-11-13
   <150> DE 196 48 625.4
   <151> 1996-11-13--.
```

Between lines 2 and 3, insert the following: -- <170> PatentIn Ver. 2.1 --.

Column 35,
Line 2, after "other", delete "stabilizing" and insert -- RNA-stabilizing --.
Line 12, after "or" insert -- into its nucleus, --.

Column 36,
Line 56, after "polyadenylation" insert -- sequence --.
Line 56, after "RNA" delete "sequence".

Column 38,
Line 32, after the first occurrence of "sequence" delete "sequence".

Column 39,
Line 20, after "to" delete "3 4" and insert -- 3 --.

UNITED STATES PATENT AND TRADEMARK OFFICE
CERTIFICATE OF CORRECTION

PATENT NO. : 6,451,593 B1
DATED : September 17, 2002
INVENTOR(S) : Burghardt Wittig and Class Junghans It is certified that error appears in the above-identified patent and that said Letters Patent is hereby corrected as shown below:

<u>Column 40,</u>
Line 2, after "to" delete "3 4" and insert -- 3 --.

Signed and Sealed this

Twenty-fifth Day of February, 2003

JAMES E. ROGAN
*Director of the United States Patent and Trademark Office*